(12) United States Patent
Dauster et al.

(10) Patent No.: US 8,998,958 B2
(45) Date of Patent: Apr. 7, 2015

(54) LOCKING DEVICE INTRODUCER INSTRUMENT

(75) Inventors: Andrew Dauster, Whitehall, PA (US); Matthew Kovach, Steamboat Springs, CO (US); Paul Weaver, Douglassville, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 1227 days.

(21) Appl. No.: 11/961,379

(22) Filed: Dec. 20, 2007

(65) Prior Publication Data

US 2009/0163962 A1    Jun. 25, 2009

(51) Int. Cl.
  *A61B 17/70*  (2006.01)
  *A61B 19/00*  (2006.01)
(52) U.S. Cl.
  CPC ......... *A61B 17/7032* (2013.01); *A61B 17/7091* (2013.01); *A61B 17/7034* (2013.01); *A61B 17/7037* (2013.01); *A61B 2019/307* (2013.01)
(58) Field of Classification Search
  CPC ................................................ A61B 17/7034
  USPC ....................................... 606/86 A, 246–279
  See application file for complete search history.

(56) References Cited

U.S. PATENT DOCUMENTS

| | | | | |
|---|---|---|---|---|
| 7,081,117 B2 * | 7/2006 | Bono et al. | ..................... | 606/300 |
| 7,780,703 B2 * | 8/2010 | Yuan et al. | ..................... | 606/246 |
| 7,780,704 B2 * | 8/2010 | Markworth et al. | .......... | 606/253 |
| 7,785,354 B2 * | 8/2010 | Biedermann et al. | ......... | 606/279 |
| 7,785,356 B2 * | 8/2010 | Biedermann et al. | ......... | 606/309 |
| 7,789,895 B2 * | 9/2010 | Heinz | ........................... | 606/246 |
| 7,789,896 B2 * | 9/2010 | Jackson | ........................ | 606/266 |
| 7,789,900 B2 * | 9/2010 | Levy et al. | ..................... | 606/300 |
| 7,794,476 B2 * | 9/2010 | Wisnewski | ................... | 606/246 |
| 7,794,477 B2 * | 9/2010 | Melkent et al. | ............... | 606/246 |
| 8,226,690 B2 * | 7/2012 | Altarac et al. | ................ | 606/256 |
| 8,551,142 B2 * | 10/2013 | Altarac et al. | ................ | 606/279 |
| 8,556,938 B2 * | 10/2013 | Jackson et al. | ................ | 606/269 |
| 2004/0138662 A1 * | 7/2004 | Landry et al. | ................... | 606/61 |
| 2004/0143265 A1 * | 7/2004 | Landry et al. | ................... | 606/61 |
| 2004/0162560 A1 * | 8/2004 | Raynor et al. | .................. | 606/73 |
| 2004/0193160 A1 * | 9/2004 | Richelsoph | ..................... | 606/61 |
| 2005/0177154 A1 * | 8/2005 | Moumene et al. | .............. | 606/61 |
| 2006/0036244 A1 * | 2/2006 | Spitler et al. | .................... | 606/61 |
| 2006/0100621 A1 * | 5/2006 | Jackson | ......................... | 606/61 |
| 2006/0142761 A1 * | 6/2006 | Landry et al. | ................... | 606/61 |
| 2006/0149233 A1 * | 7/2006 | Richelsoph | ..................... | 606/61 |
| 2006/0149241 A1 * | 7/2006 | Richelsoph et al. | ............ | 606/61 |
| 2006/0241603 A1 * | 10/2006 | Jackson | ......................... | 606/61 |

(Continued)

*Primary Examiner* — Eduardo C Robert
*Assistant Examiner* — Stuart S Bray
(74) *Attorney, Agent, or Firm* — RatnerPrestia

(57) ABSTRACT

An instrument includes components configured to secure a locking device inside a rod fixation assembly. In one embodiment, an instrument includes an outer sleeve and a pusher member arranged telescopically within the outer sleeve. A drive assembly cooperatively engages the pusher member. In another embodiment, an instrument includes an outer sleeve, a pusher member arranged telescopically within the outer sleeve, and a pair of drive assemblies. A first drive assembly engages the pusher member to distally advance the pusher member under a first loading. A second drive assembly also engages the pusher member to distally advance the pusher member under a second loading, the second loading being substantially greater than the first loading. In another embodiment, a method for reducing and locking a spinal rod includes the step of advancing a locking element while the locking element is retained in a fixed orientation.

19 Claims, 21 Drawing Sheets

(56) References Cited

U.S. PATENT DOCUMENTS

| | | | |
|---|---|---|---|
| 2006/0271047 A1* | 11/2006 | Jackson | 606/61 |
| 2007/0093817 A1* | 4/2007 | Barrus et al. | 606/61 |
| 2008/0058811 A1* | 3/2008 | Alleyne et al. | 606/61 |
| 2008/0086131 A1* | 4/2008 | Daly et al. | 606/61 |
| 2008/0086132 A1* | 4/2008 | Biedermann et al. | 606/61 |
| 2008/0086138 A1* | 4/2008 | Stone et al. | 606/72 |
| 2008/0114362 A1* | 5/2008 | Justis et al. | 606/72 |
| 2008/0114400 A1* | 5/2008 | Dant et al. | 606/246 |
| 2008/0125788 A1* | 5/2008 | Cohen et al. | 606/104 |
| 2008/0140121 A1* | 6/2008 | McLeer | 606/247 |
| 2008/0147121 A1* | 6/2008 | Justis et al. | 606/246 |
| 2008/0147122 A1* | 6/2008 | Jackson | 606/246 |
| 2008/0154308 A1* | 6/2008 | Sherman et al. | 606/265 |
| 2008/0183215 A1* | 7/2008 | Altarac et al. | 606/265 |
| 2008/0243185 A1* | 10/2008 | Felix et al. | 606/246 |
| 2010/0234891 A1* | 9/2010 | Freeman et al. | 606/266 |
| 2010/0241170 A1* | 9/2010 | Cammisa et al. | 606/264 |
| 2010/0241171 A1* | 9/2010 | Clement et al. | 606/264 |

* cited by examiner

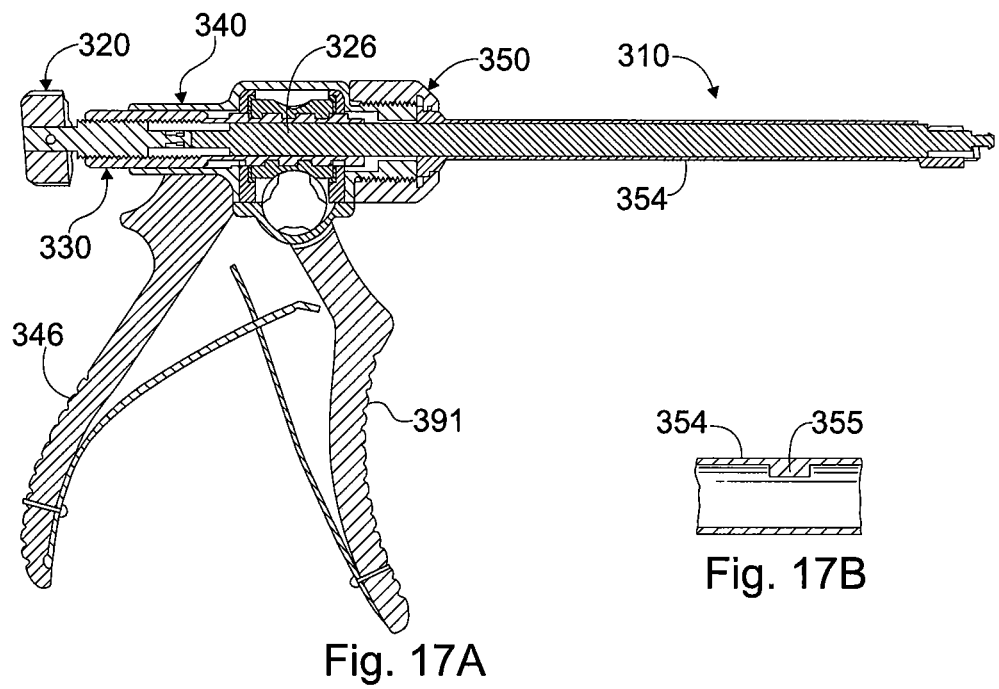
Fig. 17A
Fig. 17B
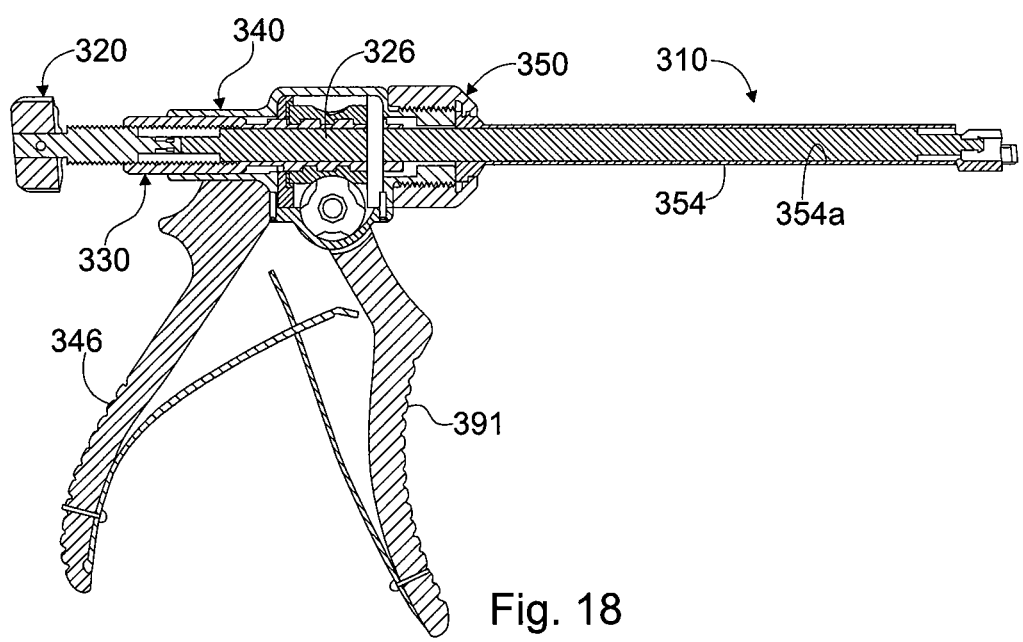
Fig. 18

LOCKING DEVICE INTRODUCER INSTRUMENT

FIELD OF THE INVENTION

The invention relates to fixation systems for the spine, and more particularly to a screw fixation system with an instrument for introducing and securing a locking element without application of torque.

BACKGROUND OF THE INVENTION

Several techniques and systems have been developed for correcting and stabilizing the spine and for facilitating fusion at various levels of the spine. Stabilization of the spine for various conditions, including degenerative disk disease, scoliosis, spondylolisthesis, and spinal stenosis, often require attaching implants to the spine and then securing the implants to spinal rods. Such spinal fixation devices can immobilize the vertebrae of the spine and can alter the alignment of the spine over a large number of vertebrae by connecting at least one elongate rod to the sequence of selected vertebrae. These rods can span a large number of vertebrae, such as three or four. The spine anatomy, however, rarely allows for three or more implants to be directly in line. In order to allow for this irregularity, the rod must be contoured to the coronal plane.

Spinal fixation has become a common approach in fusion of vertebrae and treating fractures and the above listed spinal disorders. A common device used for spinal fixation is a bone fixation plate assembly. Typical bone fixation plate assemblies have a relatively flat, rectangular plate with a plurality of apertures therethrough. Another option is an implantation fixation system that locks a rod to several vertebrae. In these system, as with other spinal fixation systems, various fasteners, such as bone screws, are used to secure the implantation fixation assembly to the desired and targeted vertebrae of the patient. These screws vary in design and shape depending upon their desired location and use.

Polyaxial locking screws are frequently used as fasteners in implantation fixation systems. Once these screws are set in a desired position, the screws must be securely fixed in that position. Movement of the screw must be minimized or eliminated. This requires a fixation system that securely engages the polyaxial screw and minimizes or prevents movement of the screw.

There are numerous polyaxial screws and fixation systems existing in the market today. Some fixation systems utilize a hollow fixing mechanism or cage having a central passage, and a polyaxial screw inserted into the central passage. The screw has a head portion that seats inside one end of the hollow fixing mechanism, and a threaded shank that projects through the end of the fixing mechanism in an exposed manner. An elongated rod is seated in the cage and extends transversely through the central passage. A threaded nut is screwed around the exterior of the cage or in the interior of the cage to lock the rod in place.

One drawback of systems that utilize set screws or other rotating locking elements is the requirement of torque to tighten or lock down the locking element. When the locking element is tightened through torque, the torque gradually transfers to the fixing mechanism and polyaxial screw. A significant amount of torque is typically applied in the final tightening. This introduces a substantial risk of "blowout", in which torque and/or other components of force tilt the shank out of its set alignment in the screw hole, causing the shank to break through the relatively thin bone wall of the pedicle. In such a case, removal and resetting of the polyaxial screw can exacerbate the trauma to the bone.

To control the risk of blowout, some practitioners use additional instrumentation to apply a countertorque to the fixation mechanism, so that the torque applied to set screw does not cause rotation or displacement of the fixing mechanism and polyaxial screw. This requires the careful balancing of torque with countertorque, and any imbalance can still cause blowout. Moreover, application of countertorque requires an additional instrument to be used at the same time that the set screw is being driven into the fixing mechanism. Aside from the obvious disadvantage of adding to instrument costs and instrument preparation, the countertorque instrument can be cumbersome to use while advancing the locking element at the same time. A surgeon who advances the set screw and holds the countertorque instrument at the same time will not have any hands free. This may compel the need for additional medical personnel during installation of the fixing assembly. The countertorque instrument further adds to the visual obstructions over the incision, and may require the size of the incision to be made larger to accommodate the additional instrumentation.

Systems that use threaded locking mechanisms are also difficult to use, requiring precise coordination and mating of components. In many cases, the assembly is very small, and proper thread starting can be difficult. If the threading is not started properly, the locking mechanism can bind, damaging the threaded surfaces and rendering the components unusable.

The foregoing drawbacks of systems secured by torque remain largely overlooked in the state of the art.

SUMMARY OF THE INVENTION

The foregoing drawbacks of fixation systems and techniques are resolved to a large degree by a fixation system and locking mechanism in accordance with the present invention.

In a first aspect of the invention, an instrument for reducing and locking a spinal rod to a rod fixation assembly includes an outer sleeve having a proximal end and a distal end, the distal end having a gripping section for engagement with a rod fixation assembly. A pusher member is arranged telescopically within the outer sleeve, and is axially displaceable within the outer sleeve but fixed against rotation relative to the outer sleeve. A drive assembly cooperatively engages the pusher member. The drive assembly is operable in a first setting to axially displace the pusher member toward the proximal end of the outer sleeve, and operable in a second setting different from the first setting to axially displace the pusher member toward the distal end of the outer sleeve.

In a second aspect of the invention, an instrument for reducing and locking a spinal rod to a rod fixation assembly includes an outer sleeve having a proximal end and a distal end, the distal end having a gripping section for engagement with a rod fixation assembly. A pusher member arranged telescopically within the outer sleeve is axially displaceable within the outer sleeve. A first drive assembly cooperatively engages the pusher member, and is configured for distally advancing the pusher member under a first loading. A second drive assembly also cooperatively engages the pusher member, the second drive assembly being configured for distally advancing the pusher member under a second loading, the second loading being substantially greater than the first loading.

In a third aspect of the invention, a method for reducing and locking a spinal rod to a rod fixation assembly includes the steps of loading a locking element into an introducer instrument in a fixed orientation relative to a longitudinal axis of the introducer instrument, attaching a distal end of the introducer instrument to the rod fixation assembly containing the rod, applying axial force to the locking element to advance the locking element while the locking element is retained in the fixed orientation along the longitudinal axis of the introducer instrument and into the rod fixation assembly to a position above the rod, displacing the spinal rod into a seated position in the rod fixation assembly, and locking the locking element in the fixed orientation within the rod fixation assembly to secure the rod in the seated position.

BRIEF DESCRIPTION OF THE DRAWINGS

The foregoing summary and following description will be better understood in conjunction with the drawing figures, of which:

FIG. 17A is a right side cross-sectional view of the instrument of FIG. 15, with components adjusted to a first position;

FIG. 17B is a truncated cross-sectional view of a component of the instrument of FIG. 15, showing details inside the component;

FIG. 18 is a right side cross-sectional view of the instrument of FIG. 15, with components adjusted to a second position;

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Fixation Assembly

Figure 1:
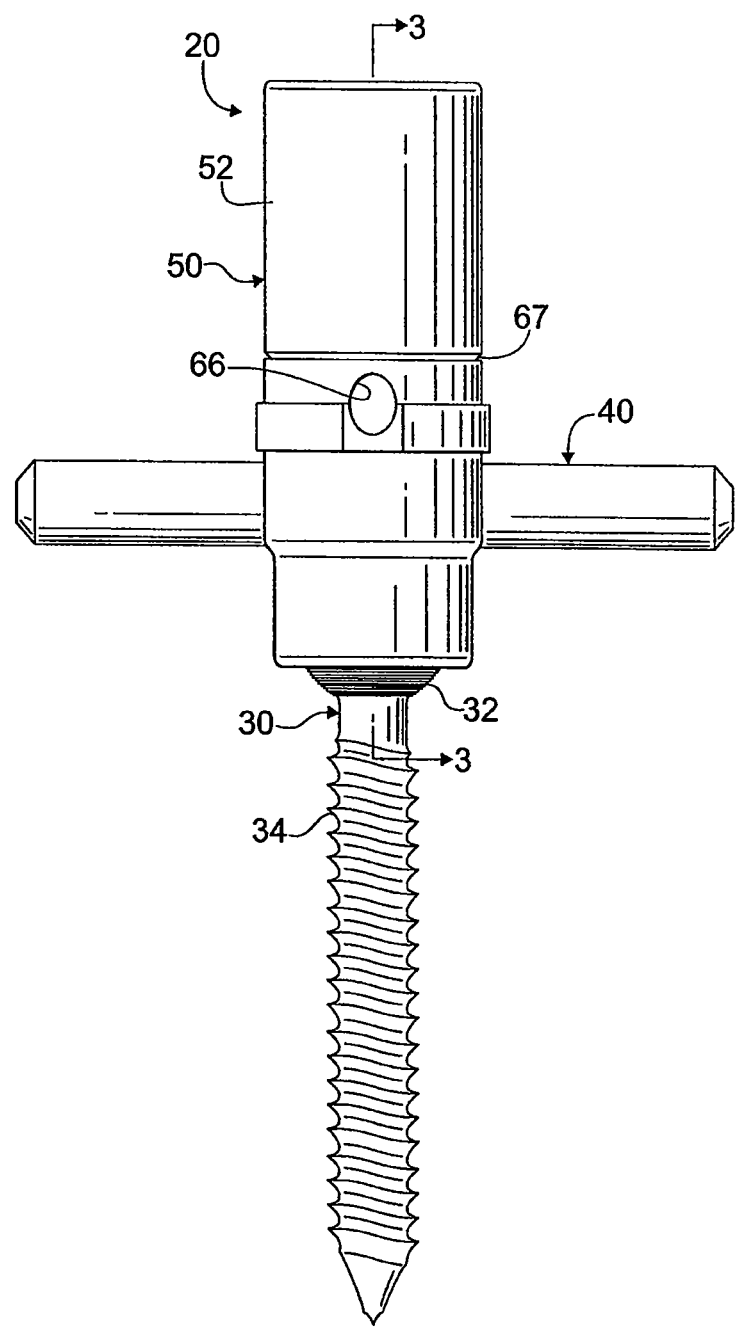
FIG. 1 is a perspective view of a screw and rod fixation assembly in accordance with a first exemplary embodiment of the present invention, viewed from a first perspective.
Figure 2:
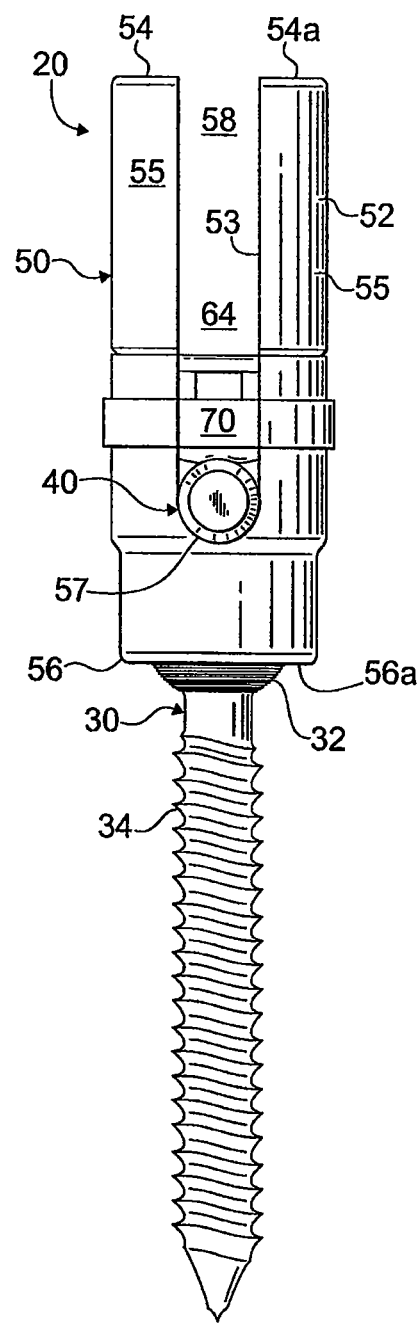
FIG. 2 is a perspective view of the screw and rod fixation assembly of FIG. 1, viewed from a second perspective.

Referring to the drawing figures generally, and to FIGS. 1 and 2 in particular, a fixation assembly 20 in accordance with an exemplary embodiment of the invention is shown. Fixation assembly 20 includes a polyaxial screw 30 and a hollow receiver component 50. Polyaxial screw 30 has a screw head 32 that is seated inside the receiver component 50, and a threaded shank 34 that projects outside the receiver component. Receiver component 50 supports a rod 40 that may be coupled to two or more polyaxial screws for stabilizing and correcting the spine at multiple levels and locations. Rod 40 is secured in receiver component 50 by a locking mechanism 70. As will be described in more detail below, locking mechanism 70 allows rod 40 to be locked securely and efficiently in receiver 50 without application of any torque or countertorque on the assembly. In addition, locking mechanism 70 allows rod 40 to be secured in multiple locked stages without application of any torque or countertorque on the assembly.

Locking mechanism 70 rigidly secures polyaxial screw 30, rod 40 and receiver body 52 together. A significant feature of locking mechanism 70 is its ability to be secured in receiver 50 without application of any torque. Another benefit of locking mechanism 70 is its ability to absorb radial stresses during insertion into receiver body 52, minimizing the potential for radial splaying of receiver body 52. Still another benefit of locking mechanism is its ability to be released or unlocked from assembly 20. These and other advantages will become more apparent in the following sections.

Fixation assembly 20 and its components are compatible with a variety of components that exist in the marketplace, making the assembly and its components advantageous in that they can be used to upgrade or replace existing assemblies and components. Upgrading and/or replacement can be implemented before, during or after an existing fixation system is installed. By way of example only, fixation assembly 20 may be used with components shown and described in the '068 patent discussed above, as well as U.S. Publication No. 2004/0193160 A1 to Richelsoph, U.S. Publication No. 2004/0162560 A1 to Raynor et al., U.S. Publication No. 2006/0149241 A1 to Richelsoph, and U.S. Publication No. 2006/0149233 to Richelsoph, the contents of which are incorporated by reference herein in their entireties.

The components of fixation assembly 20 will now be described in greater detail, with the continued understanding that the described features are merely exemplary, and are not intended to preclude other configurations from being used in accordance with the invention. Referring to FIG. 2, receiver 50 includes a hollow cylindrical body 52 having a top end 54 and a bottom end 56. Body 52 forms a central passage or bore 58 that extends between top and bottom ends 54, 56. Top end 54 includes a generally circular top opening 54*a*, and bottom end 56 similarly includes a generally circular bottom opening 56*a*.

A pair of diametrically opposed U-shaped channels 53 extend longitudinally along body 52 from top end 54 toward bottom end 56, stopping short of the bottom end. Each U-shaped channel 53 includes a rounded end 57 near bottom end 56 of receiver 50. U-shaped channels 53 are aligned with one another and form a conduit 64 extending transversely through bore 58. The width of conduit 64, and the curvature of rounded ends 57 of U-shaped channels 53, preferably conform with the dimensions and curvature of rod 40. U-shaped channels 53 are separated from one another by a pair of arms 55.

Bore 58 of receiver 50 is adapted to receive polyaxial screw 30 via an axial insertion. In a preferred embodiment, receiver 50 is a "top loaded" component. That is, the polyaxial screw and other components are inserted into receiver 50 through top opening 54*a* and advanced into bore 58. It will be understood that the direction in which components are loaded into receiver 50 is not entirely critical, and bottom loading arrangements are also possible and anticipated within the scope of the invention. For purposes of description only, a top loaded assembly will be described.

Figure 3:
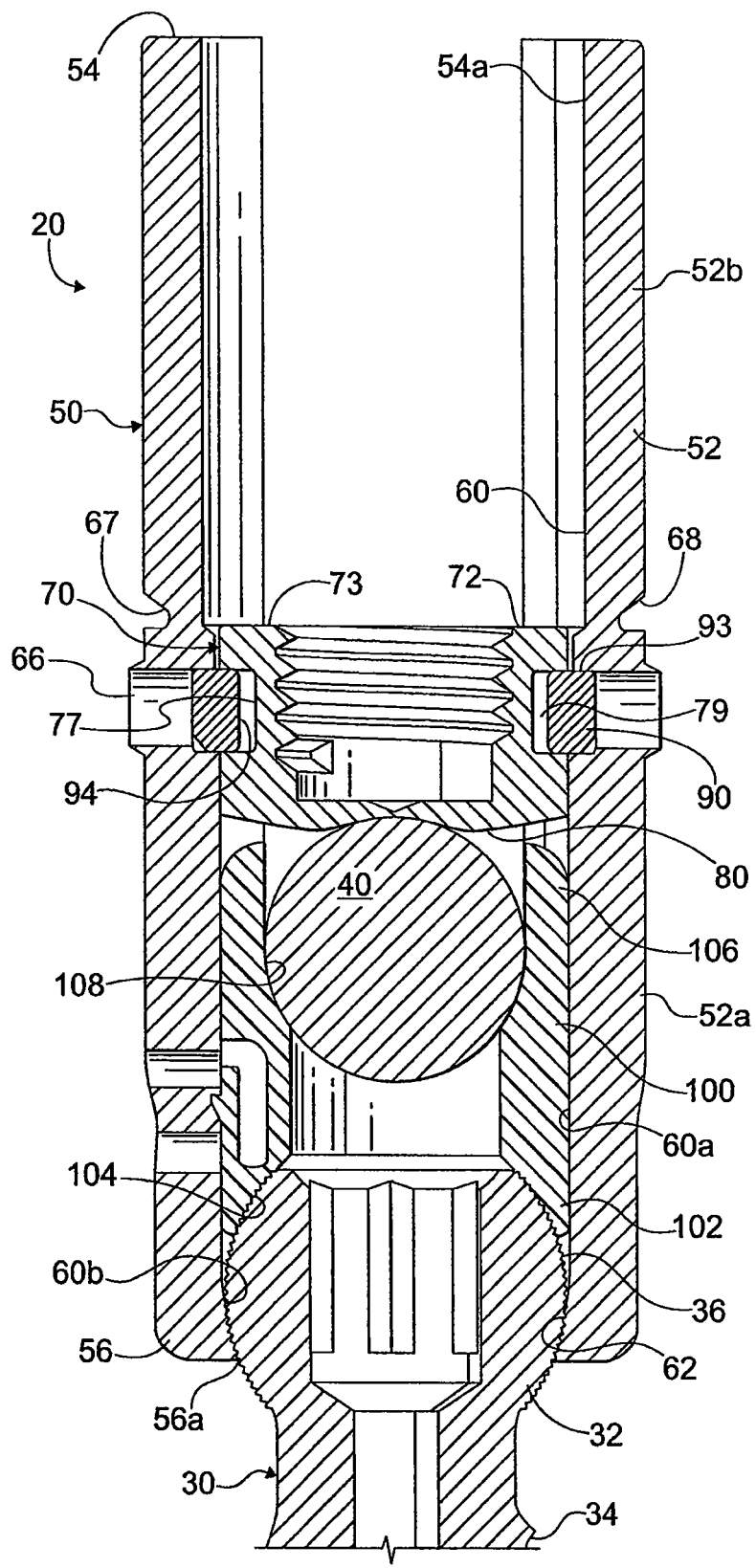
FIG. 3 is a partial cross-sectional view of the screw and rod fixation assembly of FIG. 1, taken through line 3-3 in FIG. 1, with the components shown in a locked condition.
Figure 4:
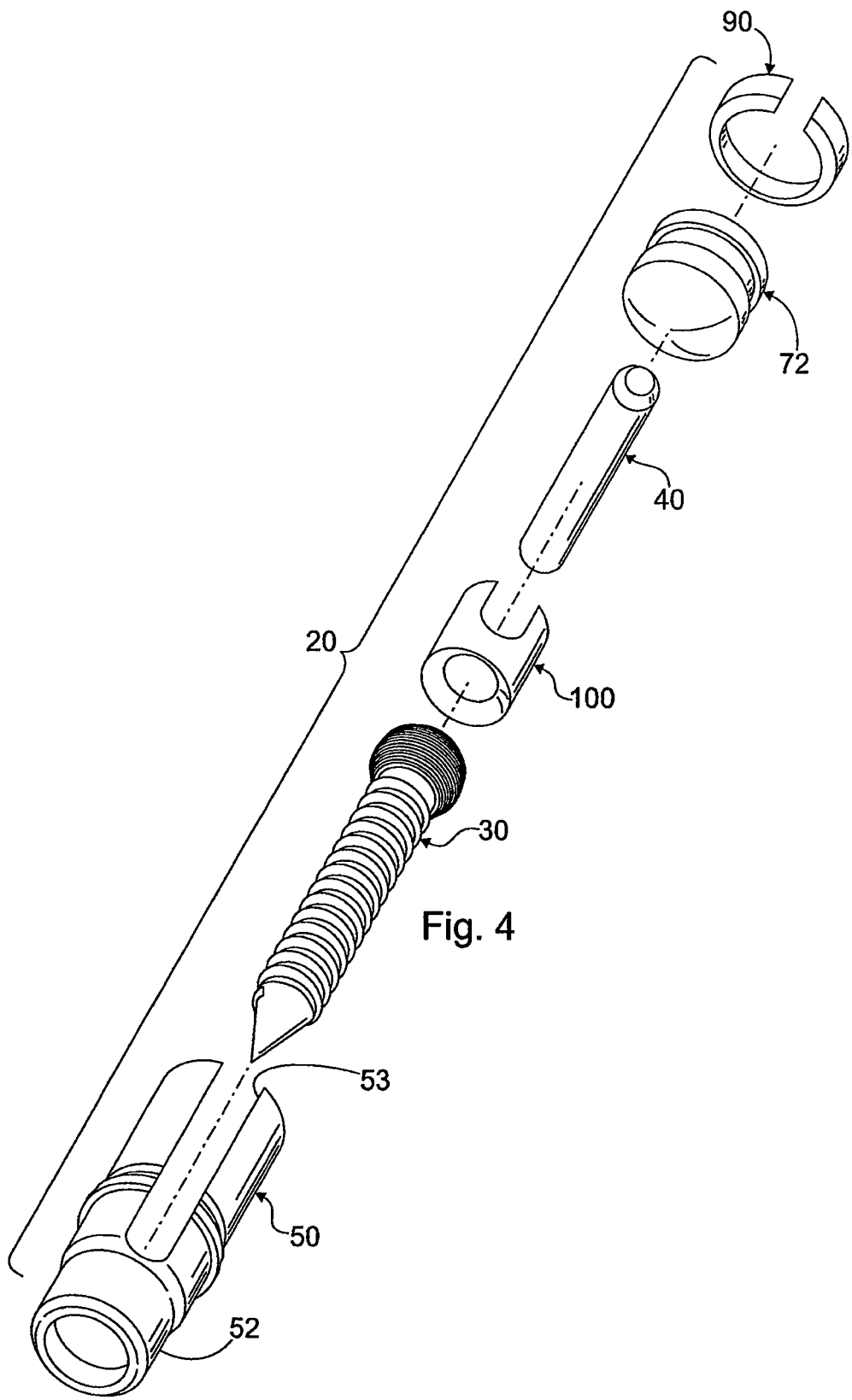
FIG. 4 is an exploded perspective view of the screw and rod fixation assembly of FIG. 1.

Referring now to FIG. 3, bore 58 is preferably cylindrical in shape like the receiver body 52, and is surrounded by an inner wall 60. Inner wall 60 permits passage of polyaxial screw 30 through bore 58, and more specifically, passage of polyaxial screw head 32. Preferably, the diameter of bore 58 is slightly larger than the maximum dimension of screw head 32 along a majority of the length of the bore. Inner wall 60 converges radially inwardly toward bottom end 56 so that bore 50 becomes slightly constricted at or near the bottom end. The restricted portion of bore 50 has a diameter that is less than the maximum dimension of screw head 32. In this arrangement, inner wall 60 forms a seat 62 that prevents passage of screw head 32 is out of bottom end 56.

Inner wall 60 may be configured a number of ways to form seat 62. For example, inner wall 60 may be tapered radially inwardly in a conical taper. In the illustrated embodiment, inner wall 60 transitions from a generally straight cylindrical geometry 60*a* to a spherically contoured section 60*b* that lies adjacent to opening 56*a* at bottom end 56. Opening 56*a* has a diameter that is greater than the maximum diameter of screw shank 34 but less than the maximum dimension of screw head 32. Therefore, opening 56*a* permits passage of screw shank 34 and a portion of screw head 32, but prevents the entire screw head from passing through the opening.

In a preferred embodiment, a rod receiving insert 100 is inserted into bore 58, immediately adjacent or above screw head 32, to strengthen the interconnection between polyaxial screw 30, rod 40 and receiver component 50. A number of axial inserts may be used in accordance with the invention, and are described in several references including but not limited to the '068 patent, U.S. Publication No. 2004/0193160 A1 to Richelsoph, and U.S. Publication No. 2006/0149241 A1 to Richelsoph, the contents of which are incorporated by reference herein in their entireties, as noted above. Insert 100 includes a bottom end 102 oriented toward bottom end 56 of receiver 50, and a top end 106 oriented toward top end 54 of the receiver. Bottom end 102 of insert 100 includes a recess 104 that receives a portion of screw head 32. Top end 106 of insert 100 includes a U-shaped rod receiving channel 108 that supports rod 40. In this arrangement, axial forces exerted on rod 40 to secure the rod in receiver 50 are transferred to insert 100 and screw head 32. Under such conditions, screw head 32 is compressed between insert 100 and seat 62.

As noted above, locking mechanism 70 rigidly secures polyaxial screw 30, rod 40 and receiver body 52 together. Locking mechanism 70 is axially inserted into bore 58 through open top end 54 of receiver 50. Although locking mechanism 70 can rotate in bore 58 during insertion and advancement into bore 58, rotation is not necessary to advance or tighten the locking mechanism into the bore. Locking mechanism 70 can include a variety of configurations for securing rod 40 in receiver 50.

Figure 5:
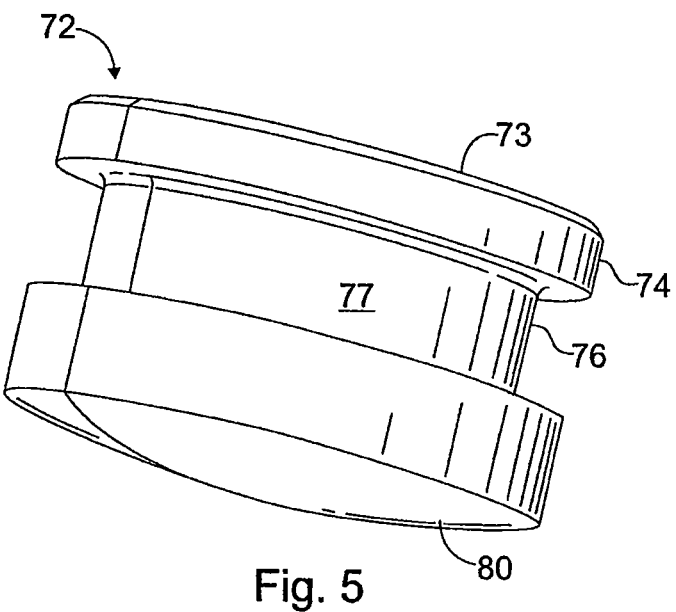
FIG. 5 is a perspective view of a first locking component in accordance with the present invention.
Figure 6:
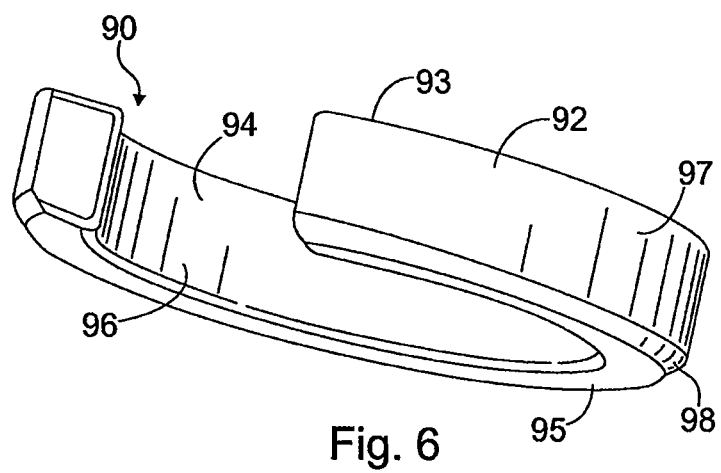
FIG. 6 is a perspective view of a first locking element in accordance with the present invention.

Referring now to FIG. 5, locking device 70 includes a generally cylindrical cap 72. Cap 72 includes a tool engaging end 73, an outer wall 74 and a rod engaging end 80. Outer wall 74 has a generally smooth surface and includes an annular recess 76 that extends radially inwardly in cap 72, terminating at an end wall 77. The diameter of outer wall 74 is slightly less than the diameter of bore 58. As will be described in subsequent sections, this arrangement allows locking mechanism 70 to be axially advanced into bore 58. Locking device 70 also includes a locking element that cooperates with cap 72. One example of a locking element is shown in the form of a locking ring 90 in FIG. 6. Locking ring 90 has a C-shaped ring body 92 formed of a resilient flexible material. C-shaped ring body 92 includes an inner face 94 and an outer face 97. Locking ring 90 forms a segment of a circle, or arc, that includes an central open section 96 surrounded by inner face 94.

Figure 7:
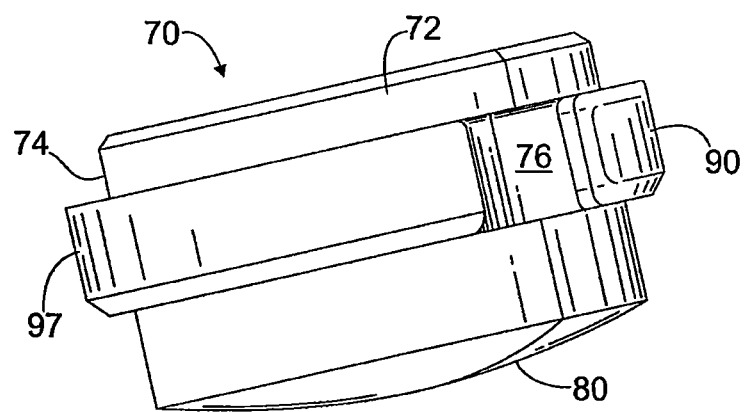
FIG. 7 is a perspective view of the first locking component of FIG. 5 and the first locking element of FIG. 6, shown in an assembled condition.

Referring to FIG. 7, locking mechanism 70 is shown with cap 72 and locking ring 90 in an assembled condition. Central opening 96 of locking ring 90 is sufficiently large to allow the locking ring to fit around the circumference of cap 72 and inside recess 76. When locking ring 90 is in a relaxed condition, an inner portion of the locking ring extends within recess 76, and an outer portion projects radially outwardly from the recess and outer wall 74 of cap 72. A small radial clearance 79 is maintained between inner face 94 and end wall 77 in groove, as shown in FIG. 3.

Locking ring 90 is radially deformable to lock and unlock locking mechanism 70 inside receiver 50. More specifically, C-shaped body 92 is elastically expandable and compressible within recess 76 so that a portion of locking ring 90 can engage with and disengage from inner wall 60 of receiver 50. C-shaped body 92 is deformable between a radially compressed condition and a radially expanded condition. In the compressed condition, locking ring 90 is pressed inwardly into recess 76, assuming a smaller diameter. In the expanded condition, locking ring 90 is extends outwardly, assuming a larger diameter. Upon being compressed, locking ring 90 stores energy that biases C-shaped body 92 radially outwardly toward a relaxed state. Locking ring 90 exhibits an outwardly directed spring bias upon being compressed, and exhibits a small amount of resistance to radial compression.

Locking ring 90 may be stretched or pulled outwardly from the relaxed state. For example, locking ring 90 may be stretched outwardly to fit the C-shaped body around the recess portion 76 of cap 72. Preferably, the material of locking ring 90 has shape memory and resilience. In this arrangement, locking ring 90 returns more or less to its original configuration when stretching force is released and the locking ring returns to the relaxed state. At least a portion of C-shaped body 92 preferably extends into recess when locking ring 90 is in the relaxed condition, so that the locking ring does not slip off cap 72.

Locking ring 90 is sufficiently flexible to compress and expand in response to engagement with inner wall 60 of bore 58 when the locking ring is inserted into receiver 50. For example, locking ring 90 is sufficiently flexible to compress inwardly in response to contacting narrow sections of bore 60. Locking ring 90 is also sufficiently resilient to expand as it aligns with wider sections of bore 60. When locking ring 90 aligns with sections of bore 60 that have a larger diameter than the diameter of the locking ring in the relaxed state, or when the locking ring is not otherwise restrained by inner wall 60, the locking ring expands within bore 58 until it reaches its relaxed state.

Locking mechanism 70 preferably incorporates a surface contour that assists in radial compression of the locking element in bore 58. Referring again to FIG. 6, locking ring 90 has a generally flat top end 93 and a contoured bottom end 95. Contoured bottom end 95 is angled with respect to the direction of axial movement so that when the bottom end contacts a constriction in bore 58, a radial component of force, i.e. a force parallel to the plane of locking ring 90, is directed into the locking ring. In this configuration, locking ring 90 will be compressed radially inwardly in response to contact with a narrow constriction in inner wall 60. A variety of contours and profiles may be used on the bottom of the locking element for this purpose. Bottom end 95 of locking ring 90 includes a beveled or chamfered edge 98 that forms an acute angle with outer face 97. It will be understood that other geometries can be used within the scope of the invention to direct a radial component of force into locking element, including but not limited to rounded edges between the bottom end and outer face, or an outer face with a diameter that gradually decreases or tapers from the top end toward the bottom end.

Figure 8:
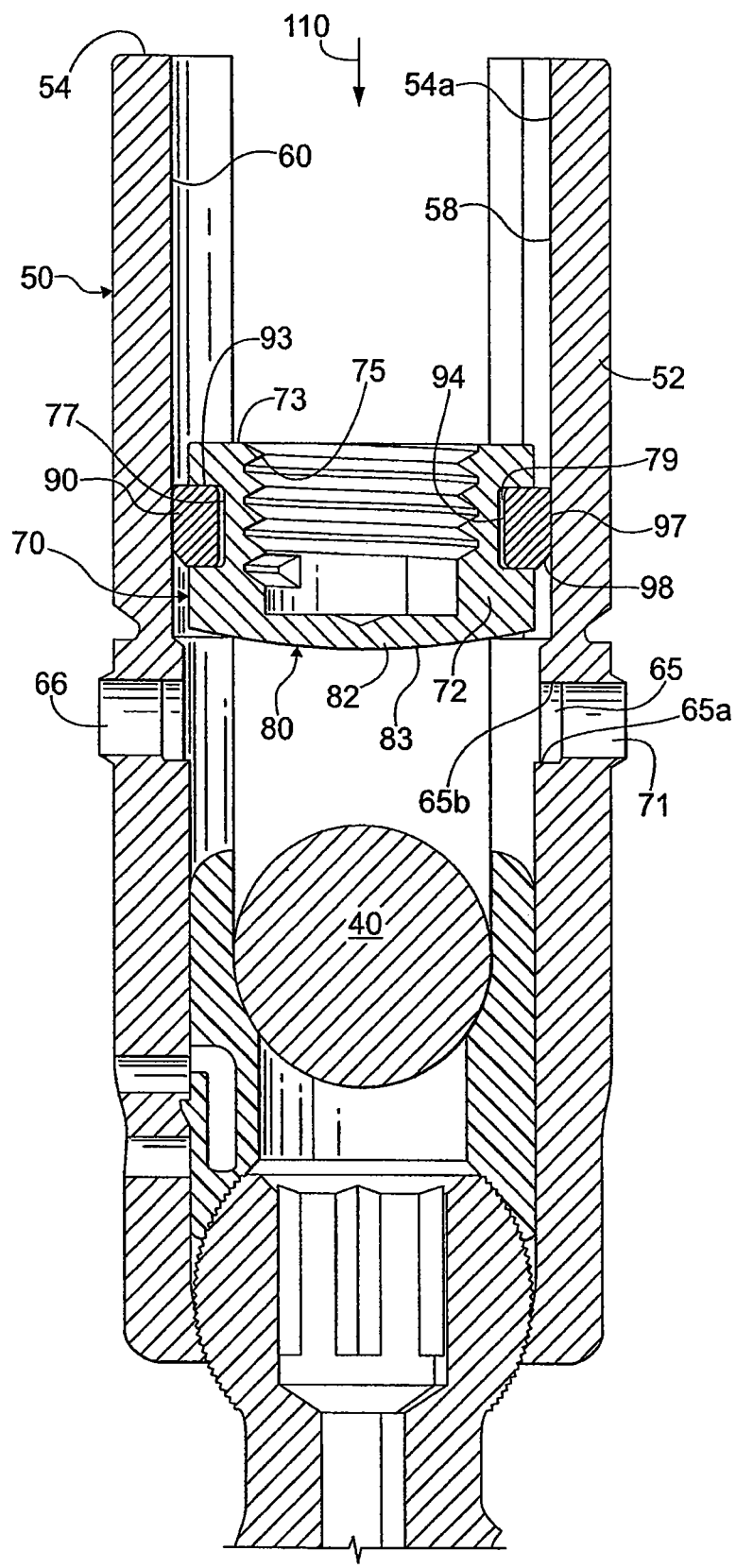
FIG. 8 is a partial cross-sectional view of the screw and rod fixation assembly components of FIG. 3, with the components shown in an unlocked condition.

Referring now to FIG. 8, the manner in which locking device 70 operates will be described. Locking element 70 is initially loaded through top opening 54a and advanced axially into bore 58 of receiver 50. The direction of axial insertion is represented by arrow 110 in FIG. 8. In a preferred embodiment, the diameter of top opening 54a and bore 58 are slightly smaller than the outer diameter of locking ring 90 when the locking ring is in a relaxed condition. When locking ring 90 is inserted into top opening 54a, the peripheral edge surrounding the top opening engages chamfered edge 98, compressing locking ring 90 radially inwardly against the spring bias. As locking ring 90 is compressed, outer face 97 is pressed radially inwardly, reducing the outer diameter or dimension of the locking ring. In addition, inner face 94 converges radially inwardly toward end wall 77 in recess 96. The radial clearance 79 in recess 96 is sufficient to receive at least a portion of locking ring 90 as the locking ring is compressed. Locking ring 90 is compressed until the diameter at outer face 97 is small enough to pass through top opening 54a into bore 58.

Energy is stored in locking ring 90 as the locking ring is compressed, biasing the locking ring radially outwardly toward its expanded state. Because the diameter of bore 58 near top opening 54a is smaller than the diameter of locking ring 90 in the relaxed state, the locking ring remains under compression as it is advanced into the bore. The outward spring bias of locking ring 90 maintains outer face 97 in constant contact with inner wall 60 during advancement, keeping the locking device centered in the bore. In this condition, which is shown in FIG. 8, locking device 70 is axially advanced in bore 58 with the outer face 97 slidably engaging inner wall 60 of the bore.

Receiver 50 includes an annular groove 65 having an axial dimension or width that is slightly larger than the axial dimension or width of locking ring 90. As locking device 70 is axially advanced into alignment with groove 65, locking ring 90 is no longer compressed or restrained at the same radial location. Locking ring 90 is free to expand under the spring bias toward the relaxed condition. In such an event, locking ring 90 springs outwardly until an outer portion of the locking ring rests inside groove 65, as shown in FIG. 3. The flat top end 93 of locking ring 90 is axially aligned with a top wall 69 of groove 69, forming an obstruction that prevents locking device 70 from being axially withdrawn from bore 58. In this condition, locking device 70 locks the axial position of rod 40 in receiver 50.

Unlike known locking mechanisms, locking device 70 does not cause radial splaying of the arms 55 as it is advanced into bore 58. The term "splaying" includes but is not limited to instances where a locking mechanism pushes the walls of the receiving member radially outwardly as it is advanced into the bore. Splaying can cause damage or weakness in the receiver body, and compromise the integrity of the receiver body's engagement with the polyaxial screw head. Severe splaying also impacts the engagement between the locking device and inner wall of the receiver, which can be especially problematic for threaded locking mechanisms. When a threaded locking mechanism becomes disengaged from the inner wall of the receiver, the locking mechanism becomes inoperable and can no longer securely lock the rod in place.

Locking mechanism 70 avoids problems associated with the "wedge effect" by absorbing radial stresses that are created as the locking mechanism is advanced into bore 58. As noted above, locking element 90 is radially compressible in response to contact with inner wall 60 of bore 58. Rather than splaying the arms 55 of receiver 50 outwardly to facilitate passage through the bore, locking element 90 yields to the inner wall 60 and contracts radially inwardly as it passes through constrictions or sections of the bore having a smaller diameter than the locking element. Arms 55 are not subject to any significant outward stress, eliminating the potential for splaying. Because splaying of arms 55 is substantially prevented, there is no need for external reinforcements on receiver body 50, such as external lock nuts or other braces that prevent outward displacement of the arms.

Referring again to FIG. 8, cap 72 has a tool engaging end 73 and a socket 75. Socket 75 is adapted to receive and engage an insertion tool through tool engaging end 73. A variety of socket shapes and configurations may be used for connection with an insertion tool, including but not limited to standard sized hexagonal sockets. In FIG. 3, socket 75 is surrounded by a threaded surface 81 for mating with a threaded surface on an insertion tool. Socket 75 does not extend partially through cap 72, stopping just before reaching rod engaging end 80. In this arrangement, a thin wall 82 is formed at rod engaging end 80.

Thin wall 82 of rod engaging end assists in locking down rod 40 in receiver body 50. In a preferred embodiment, thin wall 82 is formed of a resilient flexible material that forms a spring element at rod engaging portion 80 of cap 72. The exterior of thin wall 82 includes a convex outer surface 83. Convex surface 83 engages rod 40 when locking device 70 is set in a locked condition. Thin wall 82 is adapted to flex with elastic deformation when cap 72 is advanced into contact with rod 40. Rod 40 may also exhibit elastic deformation. Depending on the materials used and other variables, thin wall 82 and rod 40 may also exhibit plastic deformation when the rod is locked down by the locking device 70.

The thin wall 82 and rod engaging end 80 operate in the following manner to assist locking of rod 40. Locking mechanism 70 is advanced into bore 58 by axial force applied by an insertion tool. Locking mechanism 70 is advanced until rod engaging end 80 of cap 72 contacts rod 40. After rod engaging end 80 contacts rod 40, continued advancement of locking mechanism 70 will press convex surface 83 against the rod. Pressure against thin wall 82 eventually reaches a threshold limit, at which point the thin wall flexes inwardly into socket 75 under elastic deformation. When thin wall 82 elastically deforms, elastic energy is stored at rod engaging end 80. The resiliency of thin wall 82 creates a restoring force to return the thin wall to its initial convex shape. This restoring force is opposed, at least initially, by the axial force exerted by the insertion tool.

Rod engaging end 80 preferably contacts rod 40 just before locking ring 90 aligns with groove 65 in bore 58. In this arrangement, thin wall 82 will undergo elastic deformation and store energy prior to the point where locking ring 90 aligns with groove 65 and snaps outwardly into a locked condition. Once locking ring 90 snaps into groove 65, further advancement of locking device 70 is limited by the abutment between locking ring 90 and a lower wall 65a within groove 65. Axial force is released from the insertion tool, so that the restoring force in thin wall 82 is no longer suppressed. The stored energy in thin wall 82 is released to return the thin wall to its original shape prior to elastic deformation. Restoring force is exerted against rod 40, which is fixed in position relative to receiver 50. Because rod 40 does not move, the restoring force has the effect of biasing the locking mechanism 70 upwardly, or in the direction opposite the rod.

The biasing force on locking mechanism 70 pushes the expanded locking ring against an upper wall 65b of groove 65. In particular, top end 93 of locking ring 90 bears against upper wall 65b of groove. This prevents locking mechanism 70 from advancing any further toward top end 54 of receiver 50. Groove 65 is preferably arranged relative to locking device 70 such that locking ring 90 abuts the upper wall 65a of groove while thin wall 82 is still in an elastically deformed state. That is, the locking ring 90 preferably abuts upper groove wall 65a before thin wall 82 can fully return to its original convex shape. Because thin wall 82 is left in an elastically deformed condition, thin wall provides a residual biasing force against locking device 70 that rigidly secures the locking device in place.

As noted above, thin wall 82 preferably undergoes some elastic deformation prior to the point where locking ring 90 aligns with groove 65 and snaps outwardly into a locked condition. This provides an upward biasing force against locking device 70, which is created by the restoring force in thin wall 82. Thin wall 82 thus acts like a spring member that pushes and holds locking device 70 in a locked position. The amount of elastic deformation in thin wall 82, and the amount of upward biasing force, may be controlled by adjusting a number of parameters including but not limited the material of cap 72, the thickness of thin wall 82, and the axial distance between the rod-cap interface and upper wall of groove 65.

The locking device 70 will provide secure locking engagement without an upward biasing force. That is, the engagement between locking ring 90 and upper wall 65a of groove 65 is sufficient to lock rod 40 against upward displacement, without the upward biasing force. Nonetheless, providing an upward biasing force against locking device 70 will enhance the locking engagement between locking device 70 and receiver 50. Therefore, it is preferred to provide at least some upward spring force against the locking device 70. The spring force created by rod engaging end 80 is also desirable to compensate for manufacturing tolerances.

Locking mechanism 70 is advantageous in that it provides the option of a releasable lock. As with the locking operation, the procedure for releasing or unlocking the lock is accomplished without the application of torque. The lock can be taken out of the locked condition by radially compressing locking ring 90 until the ring's outer face 97 no longer extends in groove 65. A variety of configurations may be used to provide the releasable lock. Referring to FIGS. 1 and 8, receiver body 52 includes a pair of diametrically opposed release apertures 66. Each release aperture 66 is axially aligned with groove 65 and extends through the wall of receiver 50 to form an passage 71 with groove 65. In this arrangement, passages 71 provide access to locking ring 90 from the exterior of receiver 50 when the locking ring is locked in groove 65.

Passages 71 have dimensions that allow insertion and manipulation of a release tool, which is used to radially compress and unlock locking ring 90. A variety of unlocking instruments for radially compressing locking ring 90 can be imagined. For example, a tweezers-type instrument with a pair of scissor handles on one end, and an opposing pair of inwardly-facing prongs on the other end may be used. The prongs have cross-sectional dimensions that are smaller than the dimensions of apertures 66 and passages 71, and are longer than the length of the passages. The ends of the prongs can be inserted into apertures 71 and placed into contact with outer face 97 of locking ring 90. Locking ring 90 can be unlocked by inserting the prongs of the instrument into release apertures 66 so as to contact outer face 97 of locking ring 90, and squeezing the handles together to converge the ends of the prongs toward one another. The ends of the prongs apply radially inward forces against outer face 97 to radially compress locking ring 90. Radial compression is applied to locking ring 90 until the entire ring is moved out of groove 65. In this condition, the locking device 70 is unlocked or released. Locking device 70 can thereafter be axially displaced in bore 58 toward top end 54 of receiver 50, such as by engagement with a removal instrument inserted into socket 75 of cap 72, and removed from the receiver.

Figure 14:
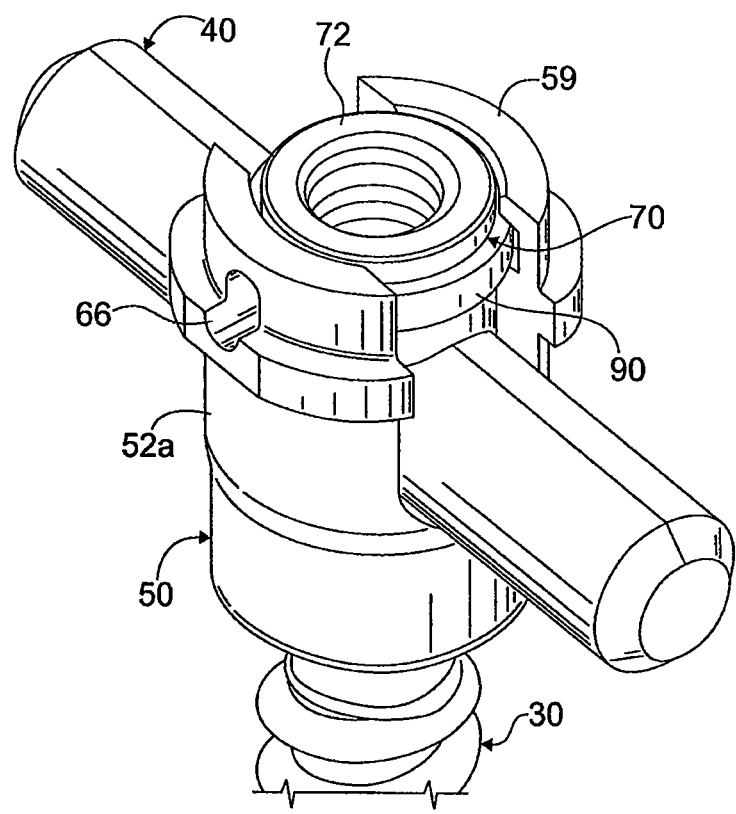
FIG. 14 is a partial perspective view of a screw and rod fixation assembly in accordance with the present invention, after a break-off portion of the assembly is removed.

In a rod reduction procedure, receiver 50 should remain relatively stable to facilitate insertion of rod 40 into bore 58. Therefore, receiver 50 preferably includes a long body 52 so that reduction instruments can securely engage receiver 50. After rod 40 is secured in its final position, the long body is no longer necessary, and may be undesirable. Rod 40 and locking device 70 are compact enough to fit within a lower portion of receiver 50, requiring only a fraction of the total length of receiver body 52. Therefore, receiver 50 preferably includes one or more thinned portions, such as thinned section 67 in FIG. 3, that allows a portion of receiver body 52 to be broken away after the rod is secured, if desired. Thinned section 67 may be configured in a number of ways to make the receiver body 52 easily breakable. In FIG. 3, thinned section 67 has a circumferential groove 68 that divides receiver body 52 into a base portion 52a below the groove, and a break-away portion 52b above the groove. In this arrangement, break-away portion 52b can be removed from receiver 50 after rod 40 has been locked. Preferably, thinned section 67 is axially positioned within a plane more or less aligned with the top end of locking device 70 when the locking device is secured in the locked position. Referring now to FIG. 14, receiver 50 is shown with the upper portion 52b removed. Lower portion 52a of receiver body 52 remains in place, with a broken edge 59 more or less coplanar with the top of locking device 70.

Referring now to FIGS. 9-12, an alternate embodiment of a locking device 170 is shown in accordance with the present invention. Many of the features shown in locking device 170 are identical to the features of locking device 70, and therefore will not be discussed. In contrast to locking device 70 described above, locking device 170 utilizes a three-component assembly comprising of a cap 172, a locking ring 190 and a spring element 182. Cap 172 has a hollow and generally cylindrical body with a rod engaging end 180. Rod engaging end 180 forms a hollow receptacle 185 for receiving spring element 182. Spring element 182 is disc-shaped and has a diameter more or less equal to the diameter of the receptacle. Rod engaging end 180 further includes a lip 187 that wraps around a bottom portion of spring element 182 to retain the spring element inside receptacle 185.

Spring element 182 is similar to thin wall 82 in that it is formed of a resilient flexible material and includes a convex outer surface 183. Convex surface 183 engages a rod when locking device 170 is set in a locked condition. Spring element 182 is adapted to flex with elastic deformation when cap 172 is advanced into contact with a rod. The resiliency of spring element 182 creates an upward biasing force against locking device 170 in the locked condition that rigidly secures the locking device in place. A number of components can be used as the spring element, including but not limited to a solid disc or Belleville washer.

Figure 9:
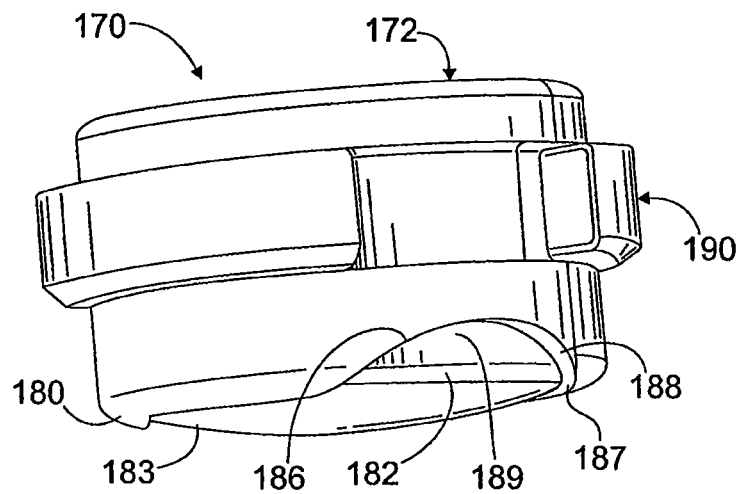
FIG. 9 is a perspective view of a second locking component in accordance with the present invention, shown in an assembled condition with the first locking element of FIG. 6.
Figure 10:
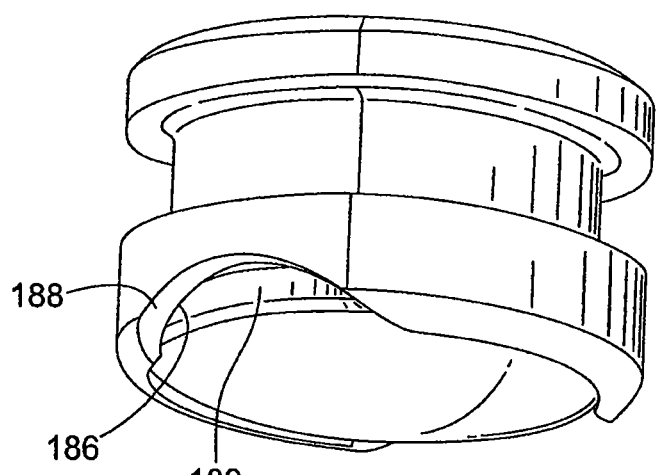
FIG. 10 is a perspective view of the second locking component of FIG. 9.
Figure 11:
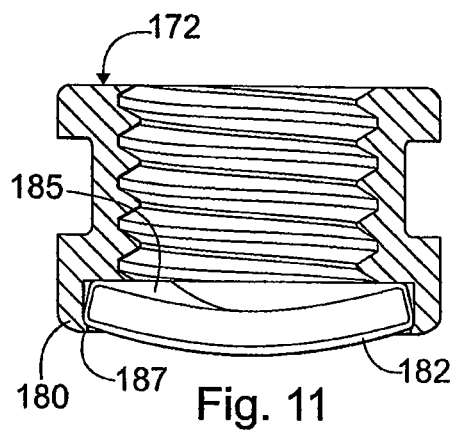
FIG. 11 is a cross-sectional view of the second locking component of FIG. 9.
Figure 12:
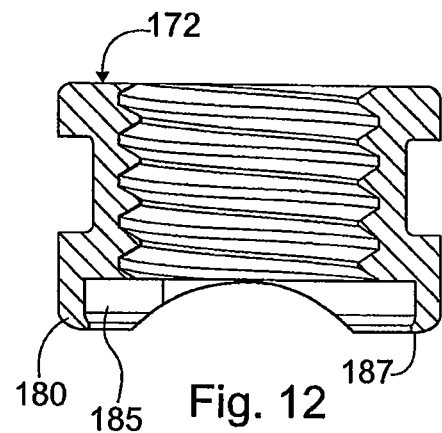
FIG. 12 is a cross-sectional view of the second locking component of FIG. 9, with a bottom part removed for clarity.

Outer convex surface 183 is recessed inside receptacle 185, with only a portion projecting out beyond lip portion 187. Rod engaging end 180 preferably includes a contoured portion to enhance the engagement between locking device 170 and the rod. In FIGS. 9 and 10, cap 172 includes a pair of diametrically opposed notches or cutouts 186 at rod engaging end 180. Each notch 186 has a generally circular profile or contour, forming a rounded edge 188. Notches 186 form an inverted channel 189 that receives the rod when outer convex surface 183 deflects. Inverted channel 189 provides a seat for the upper portion of the rod, enhancing the stability and rigidity of the locking device. The radius of rounded edges 188 is more or less equal to the radius of the rod being secured. In this arrangement, rod engaging end 180 of locking device 170 conforms to and mates with the rod's exterior, further securing the components against rotation relative to one another.

Figure 13:
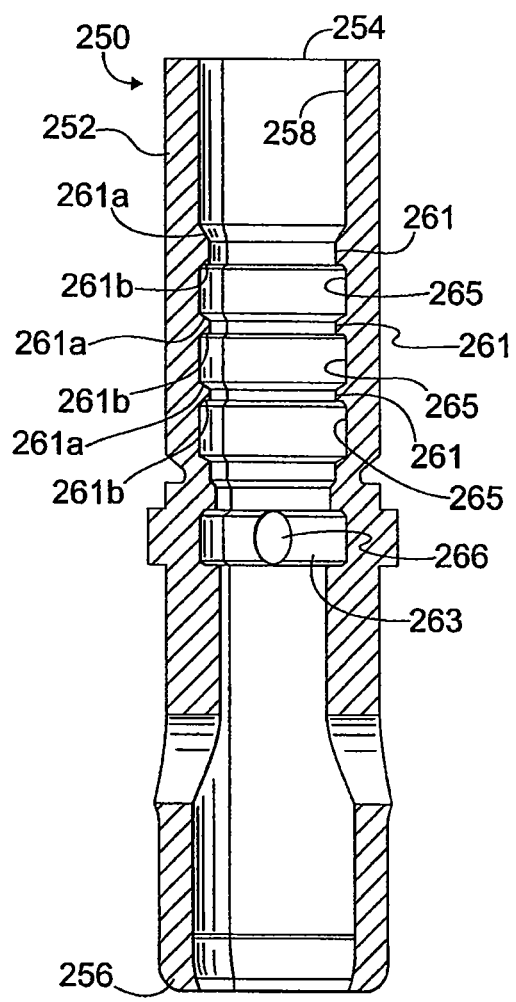
FIG. 13 is a cross-sectional view of a rod receiving component in accordance with the present invention.

Referring now to FIG. 13, a receiver 250 is shown in cross section in accordance with another exemplary embodiment. Receiver 250 is configured to permit locking of the rod in multiple positions or stages of reduction. Receiver 250 includes a generally cylindrical body 252 forming an elongated bore 258. Body 252 has an open top end 254 for receiving a locking device, such as the devices described herein. Receiver body 252 also includes an open bottom end 256 through which a portion of a fixation screw can extend. Bore 258 has a series of annular grooves 265 each defining a separate chamber for receiving a locking element, such as locking ring 90. Each groove 265 lies axially adjacent to a constriction 261. Each constriction 261 includes an annular chamfered or beveled edge 261a that forms an acute angle with the axis of receiver 250. In addition, each constriction 261 includes an edge 261b that lies generally perpendicular to the axis of receiver 250.

As locking device is advanced into receiver 250, beveled edge 261a assists in the axial progression of the locking device from a wider portion of bore 258 to a narrower portion of bore. Beveled edge 261 directs a radial component of force into the locking ring to radially compress and contract the locking ring so that the outer face of the locking ring can pass through each constriction. Once locking ring passes the constriction 261, the locking ring snaps outwardly to a locked condition, in the manner discussed previously. Perpendicular edge 261b of the constriction 261 that lies above the locking ring abuts the top end of the locking ring to prevent the locking device from moving back toward the top of receiver 250. A final locking recess 263 is aligned with a release aperture 266 to allow unlocking of the device, if desired.

Embodiments of the present invention may include a number of optional features to strengthen the locking engagement between the various components. In a preferred embodiment, for example, the exterior surface of the polyaxial screw head 32 may include a plurality of ridges 36, as shown for example in FIG. 3, to enhance the gripping engagement between the screw head and the interior of receiver 50, and the engagement between the screw head and the concave portion of insert 100. The components of the assembly may be manufactured from several different implant grade materials, including but not limited to a variety of alloys and synthetic materials. For example, cap 72 and locking ring 90 can be manufactured from cobalt chrome, and screw 30, rod 40 and insert 100 can be manufactured from titanium. The components of locking mechanisms 70, 170 may be made from the same materials or different materials. For example, cap 172 may be formed from titanium, and the spring element 182 and locking ring 190 may be manufactured from cobalt chrome. The same material may be selected for all the components, or only select components in a variety of possible combinations.

Introducer Instrument

Figure 15:
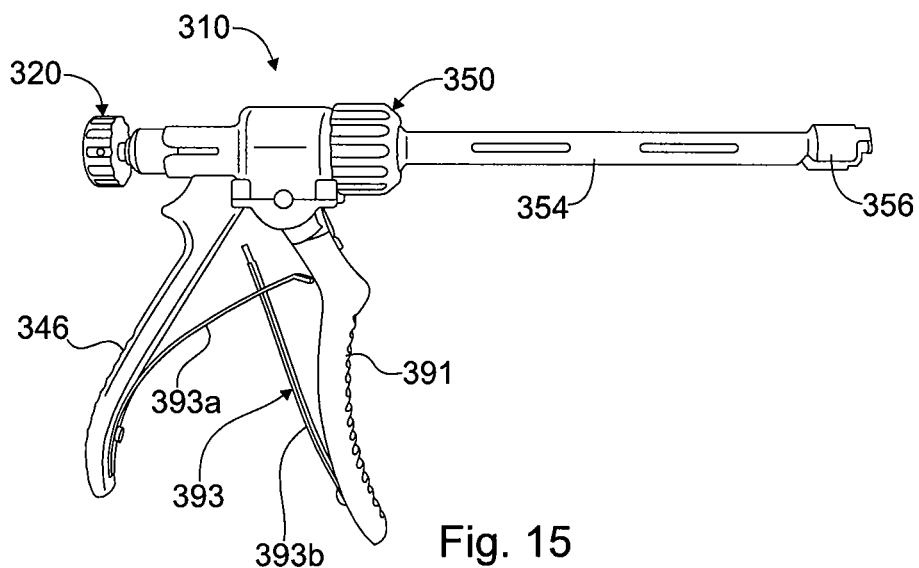
FIG. 15 is a right side view of an exemplary embodiment of an instrument in accordance with the present invention.
Figure 16:
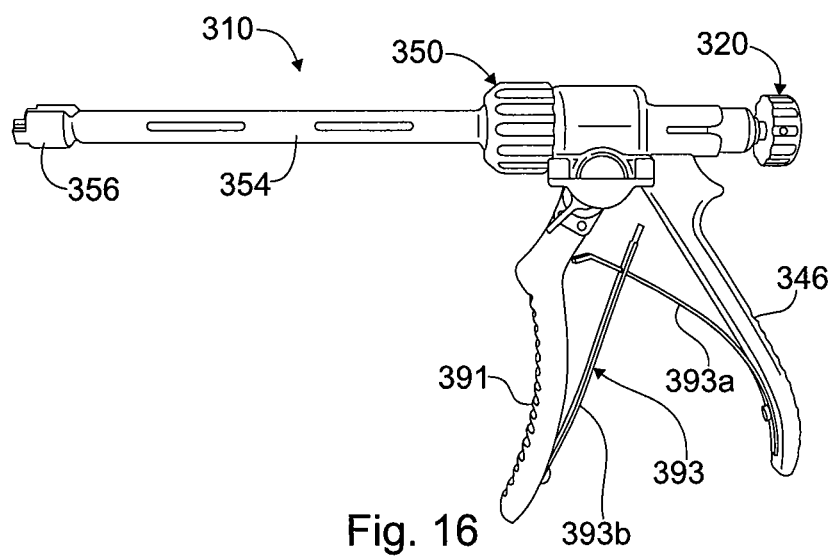
FIG. 16 is a left side view of the instrument of FIG. 15.

Referring now to FIGS. 15 and 16, an instrument 310 for introducing a locking device in accordance with one exemplary embodiment of the invention is shown. Instrument 310 is configured to secure a locking device, such as locking mechanism 70, inside a rod fixation assembly without application of any torque to the locking device, or countertorque on the assembly.

Instrument 310 includes two separate and independent drive assemblies that apply different amounts of force to the locking device during its advancement into the receiver of the fixation assembly. The locking device is secured in a compression type fit, and resistance to axial advancement can increase substantially as the locking device is moved toward a locked position. In the final stages of locking, for example, loads as high as 1200 lb or higher are applied. The separate drive assemblies include a first drive assembly to supply a relatively low loading during initial advancement of the locking device, and a second drive assembly to supply a significantly higher loading as the resistance increases. The second drive assembly incorporates a gearing system that generates a large amount of force on the locking device in response to a relatively small amount of pressure applied by the user on the instrument's handles.

Referring now to FIGS. 15-18, instrument 310 will be described in more detail. Instrument 310 includes a pusher assembly 320 having pusher shaft or member 326. The pusher member 326 is telescopically received in a nose assembly 350. Nose assembly 350 has an outer sleeve 354 with a gripping end 356 for engaging a receiver member of a fixation assembly. Pusher member 326 is axially displaceable in outer sleeve 354 to advance a locking device into a fixation assembly solely though axial displacement, and without the application of torque. A front handle 391 and rear handle 346 extend from the instrument and cooperate with other components to facilitate advancement and retraction of the pusher member 326.

Figure 19A:
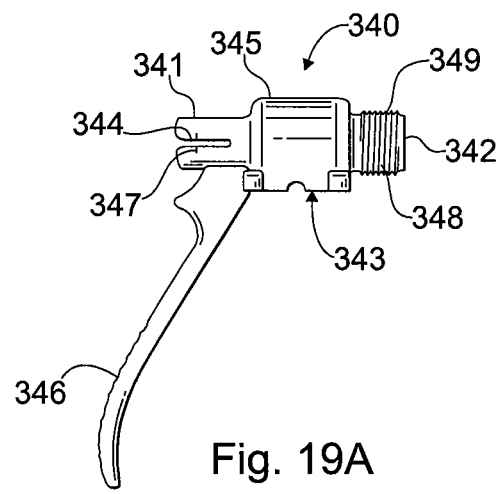
FIG. 19A is a right side view of a first assembly forming part of the instrument of FIG. 15.
Figure 19B:
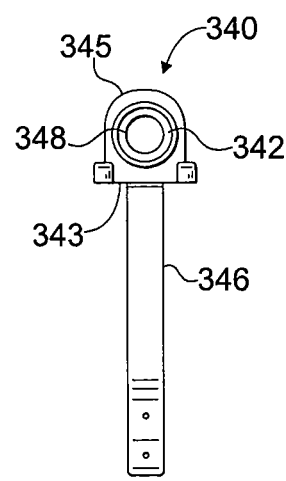
FIG. 19B is an end view of the first assembly of FIG. 19A.

Instruments in accordance with the invention are preferably assembled from a modular construction, with components that can be disassembled. This arrangement allows for sterilization and proper servicing or repair of individual parts. Instrument 310, for example, incorporates a number of different assemblies that can be disassembled and reassembled. In FIG. 19A, a rear handle assembly 340 is shown disassembled from the rest of instrument 310. Rear handle assembly 340 includes a main body portion 343 and the rear handle 346. Main body portion 343 includes a proximal end 341, a distal end 342 and a gear box 345. Preferably, main body portion 343 includes one or more indicia 347, such as laser markings for example, for purposes that will be addressed in the description of the instrument's operation. The distal end 342 includes a nose coupling 348 with an external thread 349.

Figure 20:
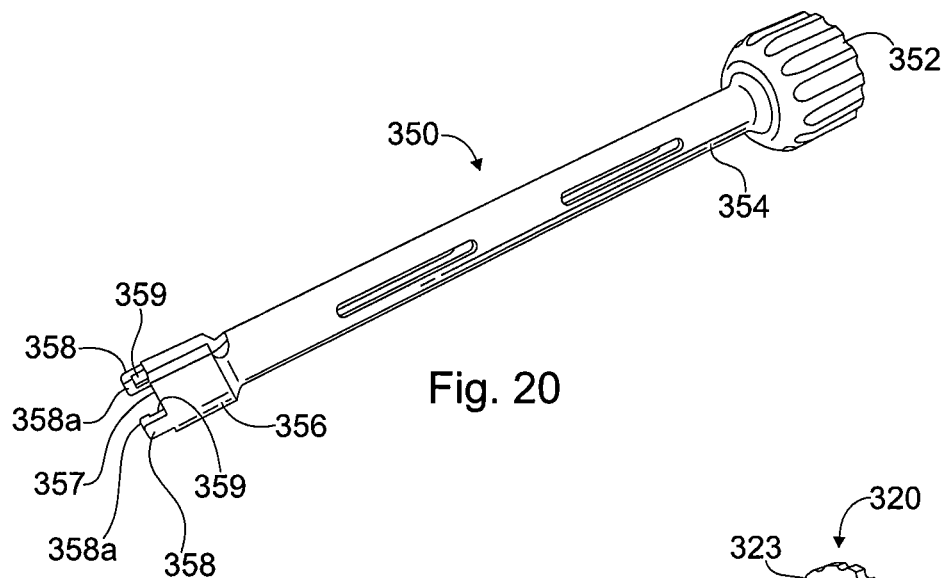
FIG. 20 is a perspective view of a second assembly forming part of the instrument of FIG. 15.
Figure 21:
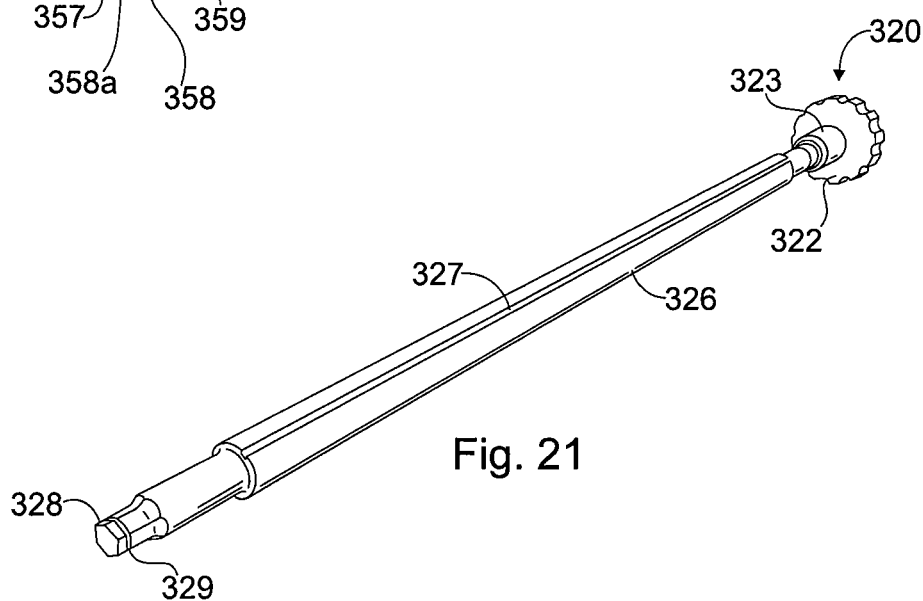
FIG. 21 is a perspective view of a third assembly forming part of the instrument of FIG. 15.
Figure 22:
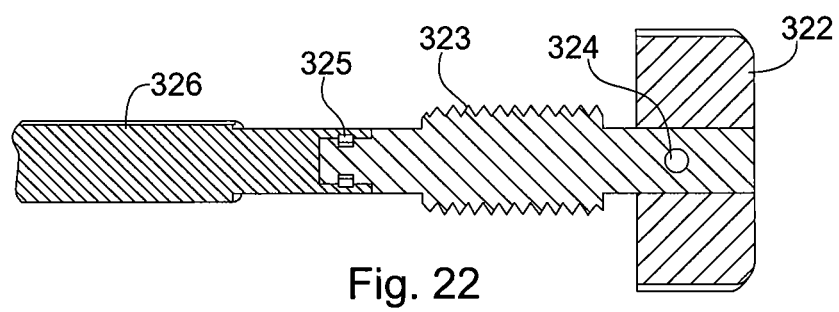
FIG. 22 is a truncated cross-sectional view of components of the third assembly of FIG. 21.

The distal end 342 of rear handle assembly 340 connects with nose assembly 350. Referring now to FIGS. 20-22, nose assembly 350 includes an attachment nut 352 having an internal thread that engages with external thread 349 on rear handle assembly 340. Nose attachment nut 352 is connected with outer sleeve 354 by a C-ring coupling or similar connection that allows the attachment nut to rotate independently of the outer sleeve. Nut 352 forms a hollow receptacle with an inner thread that engages with external thread 349 on nose coupling 348. In this arrangement, nut 352 can be threaded over nose coupling 348 and twisted to interconnect nose assembly 350 with rear handle assembly 340. The coupling between nut 352 and outer sleeve 354 allows the nut to twist independently of the orientation of the outer sleeve. The coupling also allows outer sleeve 354 to rotate relative to the entire rear handle assembly 340. During use, rear handle assembly 340 can be reoriented while the orientation of outer sleeve 354 remains fixed.

Outer sleeve 354 has a socket end 356 adapted to engage the receiver is body of a fixation assembly. Socket end 356 is hollow, forming a generally cylindrical socket 357. The diameter of socket 357 is generally equal to or slightly larger than the diameter of a receiver body to be engaged. A pair of clamping tips 358 extend distally from socket end 356. Each clamping tip 358 has an inwardly facing surface that facilitates engagement with a receiver body. A variety of surface configurations may be provided on clamping tips 358 and on the receiver body of the fixation assembly to provide a secure engagement.

Figure 33:
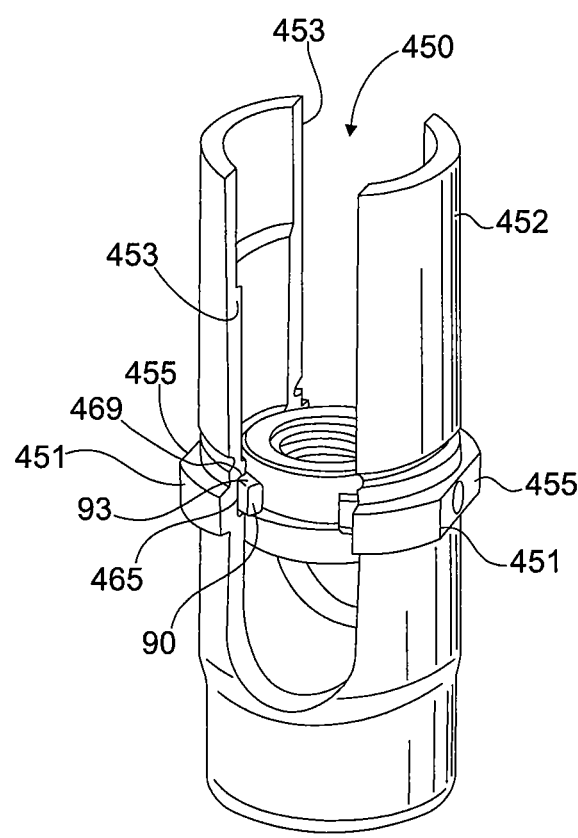
FIG. 33 is a perspective view of an exemplary receiver and exemplary locking device in accordance with the invention.

Referring now to FIG. 33, a receiver component 450 is shown in accordance with one exemplary embodiment of the invention. Receiver component 450 includes a generally cylindrical receiver body 452 and flanges 451 projecting radially outwardly from the body. Similar flanges 51 are shown on receiver body 52 in FIG. 14. Flanges 451 are divided from one another by U-shaped channels 453, and have diametrically opposed flat portions 455. Collectively, the flanges 451 form generally circular ledges that provides a secure connection with a rod reducing and/or rod locking instrument. With regard to instrument 310, flanges 451 cooperatively engage clamping tips 358. Referring again to FIG. 20, clamping tips 358 include inwardly-facing tabs 358a and recessed sections 359 adjacent to the tabs. The clearance or distance between tabs 358a is less than the diameter across the generally circular ledges at those sections of the ledges that are circular. The clearance between tabs 358a is generally equal to or greater than the dimension between flat surfaces 455, however. In this arrangement, clamping tips 358 are adapted to slide vertically over the ledges at flat portions 455. Once tabs 358a pass completely over flat surfaces 455, the tabs can be rotated beneath the rounded portions of flanges 451 until the rounded portions enter the recesses 359. In this orientation, flanges 451 are captured between clamping tips to secure instrument 310 to receiver component 450.

Referring now to FIGS. 21 and 22, pusher assembly 320 incorporates one of the instrument's two drive assemblies. In particular, pusher assembly 320 includes a round knob 322 connected with a threaded member 323 by a pin 324. Pin 324 fixes the orientation of knob 322 with respect to threaded member 323, such that the knob is rotatable in unison with the threaded member. A distal end of threaded member 323 is coupled with a proximal end of pusher member 326 by a C-ring or snap ring 325. C-ring 325 permits knob 322 and threaded pusher member 323 to rotate independently with respect to pusher member 326.

Outer sleeve 354 of nose assembly 350 has a longitudinal bore 354a that receives pusher assembly 320. Pusher member 326 is axially displaceable in bore 354a to drive a locking device into a fixation assembly. Preferably, pusher member 326 and outer sleeve 354 have an alignment feature that retains the pusher member in a fixed orientation with respect to outer sleeve 354, preventing the pusher member from rotating relative to the outer sleeve. The reasons for this alignment feature will become clearer from the descriptions that follow. To this end, the wall along bore 354a preferably includes a projection that extends radially inwardly. The projection may be an elongated tab or a relatively small boss that projects from the inner wall of bore 354a. Referring to FIG. 17B, the inner wall includes a small guide tab or key 355. Pusher member 326 has a longitudinal channel on its exterior forming a keyway 327 that corresponds to the key 355. Key 355 aligns with and extends within keyway 327 when pusher member 326 is inserted into outer sleeve 354, substantially preventing the pusher member from rotating with respect to the outer sleeve.

A distal end or tip 328 of pusher member 326 is shaped to engage the interior of a locking component. Tip 328 may include a number of configurations, such as an external thread or, as shown in FIG. 21, a hexagonal end. It will be noted that a threaded configuration requires a rotation of pusher member 326 with respect to a threaded locking device, such as device 70. Nonetheless, this rotation is not applied during reduction of the rod or locking of the locking device, but rather before rod reduction and locking. Prior to connecting the instrument with a receiver body, distal tip 328 can be extended out of the distal end of outer sleeve 354 to expose the distal tip and thread a locking device onto the distal tip. Once the locking element is threaded to the distal tip of the pusher member, the pusher member and locking element are locked into a receiver body by application of axial force on the pusher member. Therefore, the threaded configuration does not require application of torque to the fixation assembly itself and therefore does not pose the potential risks discussed above when torque is otherwise applied during rod reduction and locking.

Preferably, the locking device has a hexagonal hole or similar non-threaded connection so that the pusher member can be coupled with the locking device without rotation. In the illustrated embodiment, pusher member 326 includes a retaining ring 329 adapted to snap into an internal recess or groove inside a locking element to allow a snap connection with axial advancement of the pusher member, and without twisting or rotating the pusher member. With this arrangement, a locking device can be easily snapped onto the end of pusher member 326 either manually, or using a cartridge type loading mechanism.

Instruments in accordance with the present invention can be used with a variety of locking element configurations, including locking elements that are secured by the action of resilient locking rings, like locking device 70. Where locking rings like locking ring 90 are used, the position of the opening or split in the locking ring can influence the strength of the locking engagement with the receiver. The strongest connection may be achieved when the split in ring 90 is aligned with one of the U-shaped rod receiving openings of the receiver body. This type of alignment is illustrated in FIG. 33. With the split aligned with a U-shaped opening, a maximum amount of surface area on top end 93 of locking ring 90 is aligned with a top wall 469 of groove 465, so as to maximize the area of obstruction that prevents the locking device from being axially withdrawn from the receiver.

Because the orientation of the locking ring can be significant, the instrument preferably includes a mechanism for controlling the relative position of the locking ring during axial advancement and placement of a locking device into a fixation assembly. The keyway 327 on pusher member 326 provides one aid for setting and controlling the alignment of a locking ring. In a preferred embodiment, keyway 327 and key 355 in outer sleeve 354 are positioned within a plane extending through the center lines of front handle 391 and rear handle 346. By attaching locking device 70 to pusher member 326 with the split aligned with keyway 327 and key 355, the relative orientation of locking ring 90 inside outer sleeve is maintained within the plane of the handles. The user is therefore aware of the orientation and position of the split prior to advancing the locking device.

Clamping tips 358 are arranged with respect to handles 391, 346 so that the handles and the split in locking ring 90 align with the rod after socket end 356 is twisted to the secured position over ledges 451. Referring now to FIG. 15, clamping tips 358 are offset from the plane of the handles by an angle of 30 degrees. In this configuration, socket end 356 is initially lowered over flat surfaces 455 with the handles out of alignment with the rod. Upon twisting the instrument to secure is clamping tips 358 over ledges 451, the handles are pivoted approximately 30 degrees. The user knows that the receiver is completely engaged within clamping tips 358 when handles 391, 346 align with the rod. The split in locking ring 90 aligns with the U-shaped openings in the receiver as the clamping tips 358 are twisted to the secured position.

Figure 27:
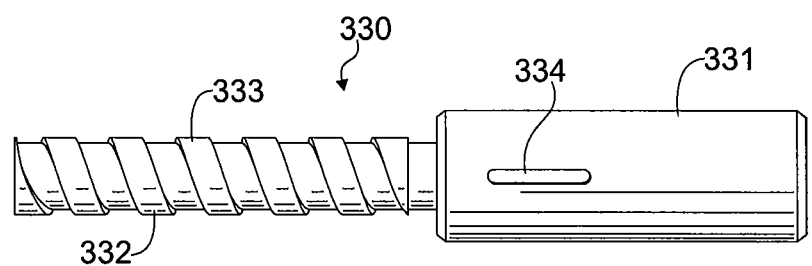
FIG. 27 is a side view of the load shaft shown in FIG. 23.
Figure 28:
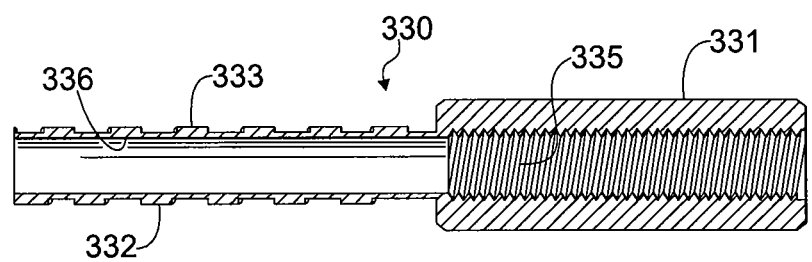
FIG. 28 is a cross-sectional side view of the load shaft shown in FIG. 27.

Referring again to FIGS. 17A and 18, pusher assembly 320 is surrounded by a load shaft 330. Load shaft 330 is axially displaceable within rear handle assembly 340 and facilitates axial displacement of pusher member 326. FIGS. 27 and 28 show the features of load shaft 330 in more detail. Load shaft 330 is generally cylindrical and includes a proximal section 331 and a distal section 332. A bore 336 extends longitudinally through load shaft 330. Proximal section 331 has a substantially smooth exterior and an internal thread 335 along bore 336. The smooth exterior of proximal section 331 has two diametrically opposed alignment tabs 334. Rear handle assembly 340 features a corresponding pair of alignment slots 344 that receive alignment tabs 334. Slots 344 are elongated to allow axial displacement of load shaft 330 relative to rear handle assembly 340. The width of slots 344 is only slightly greater than the width of tabs 334, however. In this arrangement, alignment slots 344 permit axial displacement of load shaft 330 within rear handle assembly 340 while substantially preventing rotation of the load shaft relative to the rear handle assembly. Distal section 332 of load shaft 330 has a reduced diameter relative to proximal section 331, and a substantially smooth surface along bore 336. The exterior of reduced diameter section 332 has an external power thread 333.

As noted above, instrument 310 features two independently operating drive assemblies for driving a locking element into the receiver of a rod fixation assembly. Each drive assembly cooperates with load shaft 330 to facilitate axial displacement of pusher member 326. The first drive assembly which was described above includes threaded pusher member 323 in conjunction with load shaft 330. The external thread on threaded pusher member 323 cooperatively engages internal thread 335 in proximal section 331 of load shaft 330. In this arrangement, threaded pusher member 323 is axially displaceable in bore 336 of load shaft 330 in response to rotation of knob 322. Preferably, the threads are arranged such that threaded pusher member 323 is driven toward distal end 342 of rear handle assembly 340 when knob 322 is rotated in a clockwise direction from a user's perspective. Pusher member 326, in turn, is driven toward the distal end of outer sleeve in response to axial displacement of threaded pusher member 323. Torque applied to knob 322 is transferred to threaded pusher member 323, but is not transferred past snap ring 325 to pusher member 326. As a result, pusher member 326 moves axially within outer sleeve 354 without undergoing torque. In the preferred instrument, pusher member 326 remains in a fixed orientation by the engagement between keyway 327 and key 355.

Figure 23:
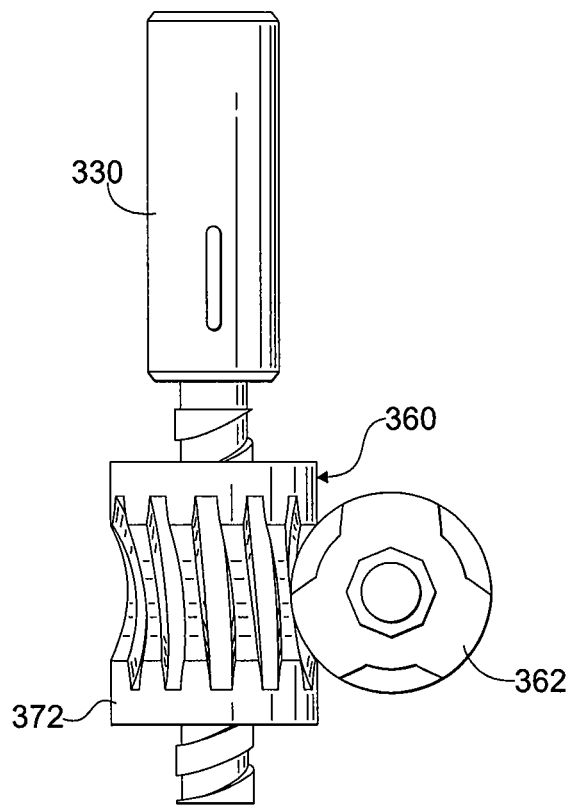
FIG. 23 is a truncated side view of interconnected components of the instrument in FIG. 15, including a worm, a worm gear and a load shaft.
Figure 24:
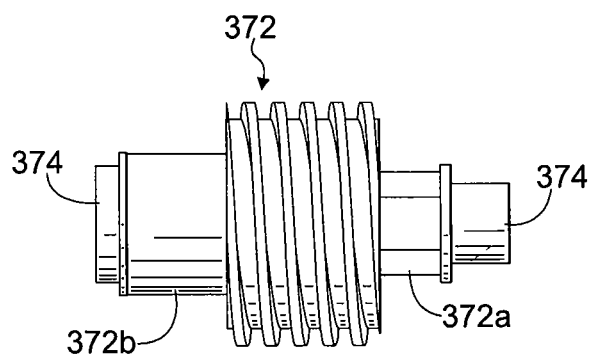
FIG. 24 is a side view of the worm shown in FIG. 23.
Figure 25:
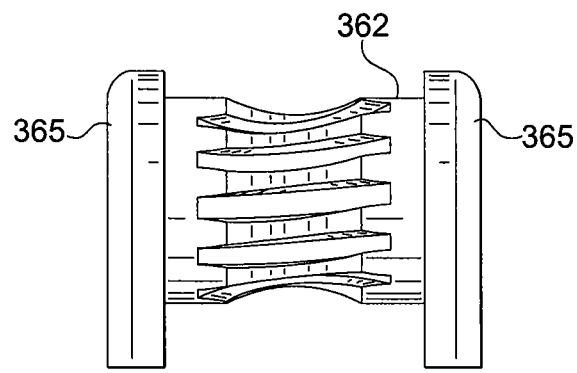
FIG. 25 is a side view of the worm gear shown in FIG. 23 and associated components.
Figure 26:
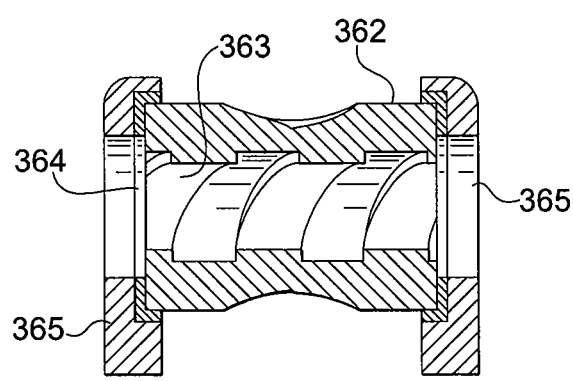
FIG. 26 is a cross-sectional side view of the components of FIG. 25.
Figure 29:
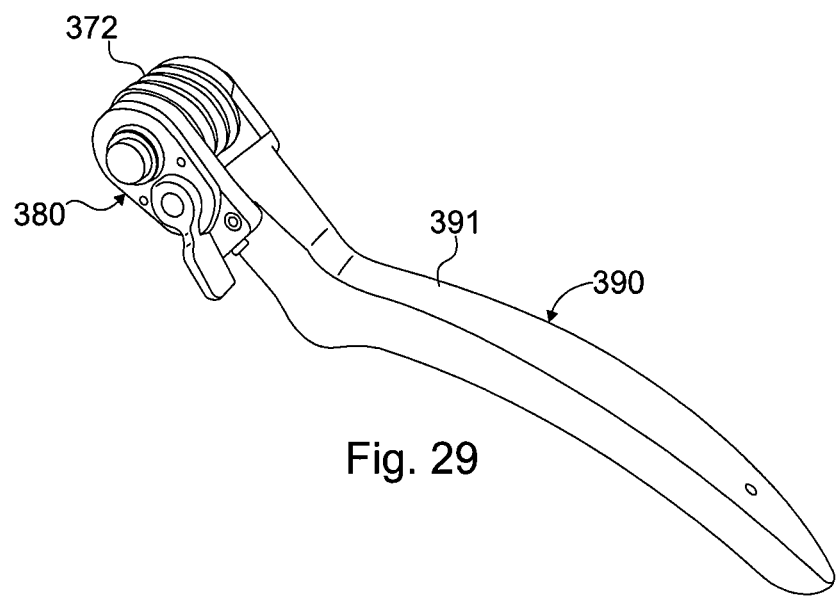
FIG. 29 is a perspective view of the worm shown in FIG. 23 assembled with additional components of the instrument of FIG. 15.
Figure 30:
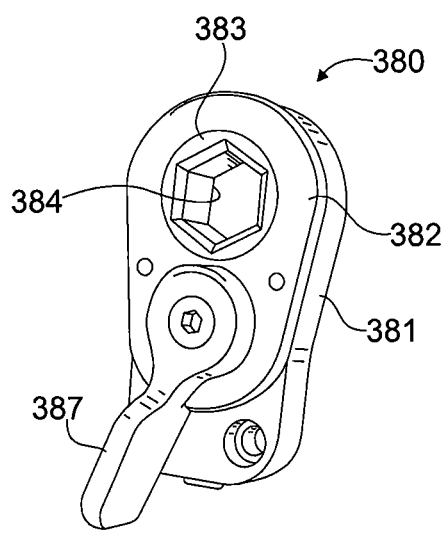
FIG. 30 is a perspective view of a fourth assembly of the instrument shown in FIG. 15.

The second drive assembly includes a gear assembly 360 and a front handle assembly 390. Referring now to FIG. 23, the components of gear assembly 360 are shown connected with load shaft 330. Gear assembly 360 includes a worm gear 362 in operable engagement with a worm 372. Worm 372 is connected with front handle assembly 390, as shown in FIG. 29. A pair of pin members extend from each side of worm 372, as shown in FIG. 24. A first pin member 372a has a hexagonal configuration, and a second pin member 372b has a cylindrical configuration. A pair of inserts 374 extend from each end of worm 372. Referring to FIGS. 25 and 26, worm gear 362 is mounted between a pair of bearing bodies 365 that extend within gear box 345. A pair of bearing surfaces 364 are pressed into bearing bodies 365. Bearing surfaces 365 allow worm gear 362 to spin freely between the bearing bodies, while retaining worm gear in a fixed axial position relative to gear box 345. Worm gear 362 includes a bore and an internal power thread 363 extending in the bore. Internal power thread 363 engages external power thread 333 of load shaft 330. In this arrangement, rotation of worm gear 362 causes load shaft 330 to move axially in the rear handle assembly 340. Rotation of load shaft 330 is substantially prevented by the engagement of alignment tabs 334 with alignment slots 344.

Referring to FIGS. 29-32, front handle assembly 390 includes a ratchet assembly 380 and a front handle lever 391. Ratchet assembly 380 is operable to control the directional displacement of worm 372 in response to movement of handle lever 391. Generally, ratchet assembly 380 is operable in two modes: a first mode to move pusher member in a proximal direction in response to movement of handle lever 391, and a second mode to move pusher member in a distal direction in response to movement of the handle lever. In this arrangement, ratchet assembly 380 can be set to either advance pusher member or to retract the pusher member in outer sleeve 354.

Ratchet assembly 380 includes a hollow ratchet body 381 and a cap 382. Ratchet body contains a bi-directional ratchet wheel 383 forming a hex hole 384 centrally located on the ratchet wheel. Hex hole 384 receives hexagonal pin member 372a on worm 372. Ratchet wheel 383 includes a plurality of teeth that engage a pawl 385. Pawl 385 has two sets of teeth 385a that engage with teeth on ratchet wheel 383. In addition, pawl 385 has a disc-shaped body portion 385b that is pivotably mounted on a central hub. Body 385b has a pair of irregularly-shaped pockets 385c symmetrically arranged on the perimeter of pawl 385. A toggle lock 386 with a ball-shaped end 386a slidably engages disc-shaped body 385a at pockets 385c. The radius of ball-shaped end 386a is such that the ball-shaped end generally fits into each pocket 385c.

Figure 31:
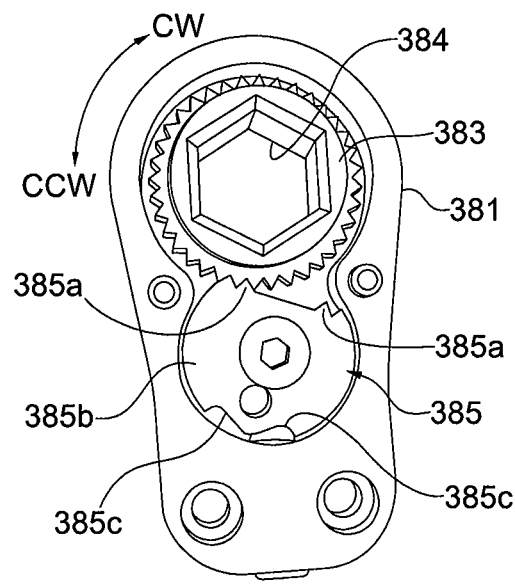
FIG. 31 is a perspective view of the fourth assembly of FIG. 30 with certain components omitted to illustrate internal components of the fourth assembly.
Figure 32:
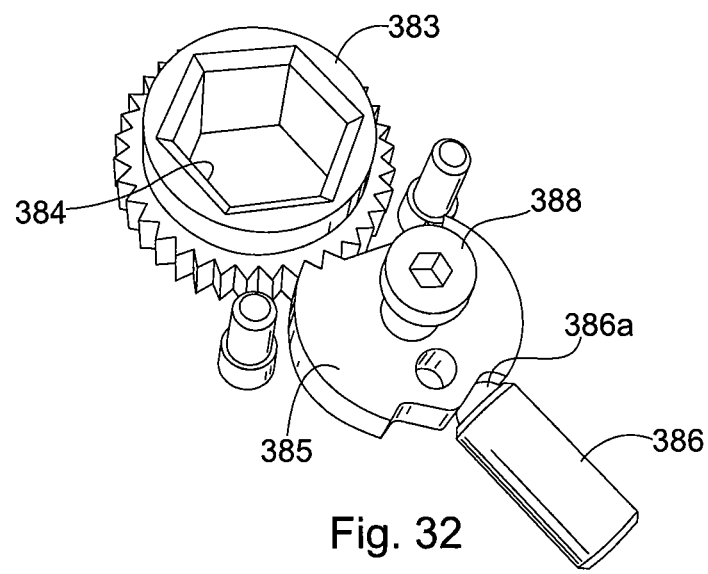
FIG. 32 is a perspective view components of the fourth assembly of FIG. 30 shown disassembled.

The range of pivot motion of disc-shaped body 385b is limited by the engagement between toggle lock 386 and pockets 385c. Disc-shaped body 385b is permitted to pivot or tilt between a first orientation, in which the toggle lock 386 engages a one pocket, as shown in FIG. 31, and a second orientation, in which the toggle lock engages the other pocket. In this arrangement, ratchet assembly 380 generally, and pawl 385 in particular, can be toggled between two settings. In the setting shown in FIG. 31, toggle lock 386 is engaged with the right-side pocket and prevents ratchet wheel 383 from rotating in a counterclockwise direction, represented by arrow "CCW". In this setting, toggle lock 386 substantially prevents body 385b from rotating any further in the clockwise direction, represented by arrow "CW." Toggle lock 386 does allow body 385b to rock slightly in the counterclockwise direction, however, in response to a clockwise torque applied to ratchet wheel 383. The counterclockwise rocking of pawl 385 allows the teeth on wheel 383 to pass clockwise over the set of pawl teeth 386a on the left side. The engagement between ball-shaped end 386a and the right pocket 385c becomes less and less stable as the pawl is rocked, until the ball-shaped end forces pawl 385 to reverse direction, allowing the ball-shaped end to return to the more stable position within the pocket. The pawl returns to the position shown in FIG. 31, with the first set of pawl teeth 386a fully engaged with the ratchet wheel teeth. Torque transferred from ratchet wheel 383 to pawl 385 is generally not strong enough by itself to overcome the resistance offered by toggle lock 386 and move ball-shaped end 386a out of the pocket.

Ratchet assembly 380 can be toggled out of the setting shown in FIG. 31 to an alternate setting which allows ratchet wheel 383 to rotate in the counterclockwise direction. The setting of ratchet assembly 380 can be changed by displacing a switch lever 387 that extends outside ratchet body 381. The hub on which pawl 385 pivots includes a screw 388 that connects the pawl to the switch lever 387. Switch lever 387 is pivotable in unison with pawl 385 between a first position, in which the left-side pawl teeth engage ratchet wheel 383, and a second position, in which the right-side pawl teeth engage the ratchet wheel. In this arrangement, switch lever 387 toggles the ratchet assembly 380 between two settings that control the direction of ratchet wheel 383.

The ends of worm 372 act like a hinge connection for forward handle 391, which is pivotable about an axis passing through the worm, as shown in FIGS. 15 and 16. Forward handle 391 pivots between a ready position, in which the handle is positioned toward the distal end of the instrument, and a compressed position, in which the handle is squeezed or pulled proximally toward the rear handle 346. Forward handle 391 and rear handle 346 are interconnected by a return spring mechanism 393 that biases the forward handle 391 toward the ready position. Return spring mechanism 393 comprises a pair of spring members 393a, 393b that urge the forward and rearward handles 391, 346 apart when the spring members are under no load. Spring members 393a, 393b are compressible when forward and rearward handles 391, 346 are squeezed together, and expand outwardly and away from one another when pressure is released from the handles. In this arrangement, return spring mechanism 393 is operable to return forward handle to a forward position after forward handle is squeezed and released.

The general operation of instrument 310 will now be described in greater detail, with reference to locking device 70. As an initial step, locking device 70 is attached onto pusher member 326. Pusher member 326 may be extended past the distal end of outer sleeve 354 of nose assembly 350 to allow the locking element to be loaded onto the pusher member's distal end. Alternatively, the entire pusher assembly 320 can be pulled out of the rear end of rear handle assembly 340 by twisting knob 322 and unscrewing threaded pusher member 323 from load shaft 330. Locking device 70 is then threaded or snapped onto the distal end of pusher member 326, depending on the type of connection used on the locking device.

Locking device 70 is attached to pusher member 326 with the split aligned with keyway 327 and key 355. Because keyway 327 and key 355 prevent pusher member 326 from rotating relative to outer sleeve 354, the orientation of locking ring 90 will remain substantially fixed inside the outer sleeve. To prepare instrument 310 for attachment to receiver member, pusher member 326 is preferably moved to a fully retracted position in the outer sleeve. As noted above, main body 343 preferably includes laser markings or other indicia that align with a specific section on load shaft 330 to alert the user that load shaft 330 is fully retracted. For example, main body 343 may include markings that align with the proximal ends of the alignment tabs 334 when load shaft 330 is fully retracted.

Once load shaft 330 is fully retracted, the user can continue to retract pusher shaft 326 by actuating the first drive assembly via twist knob 322. Knob 322 may be rotated, preferably in a counterclockwise direction from the user's perspective, to unscrew threaded pusher member 323 and retract pusher member 326 to the fully retracted position.

After pusher member 326 is fully retracted, ratchet switch is moved to the forward or "drive" setting to prepare the instrument for introducing the locking device. At this time, a spinal rod is placed within the rod receiving slot of a receiver member, such as the U-shaped channels of receiver member 450. Socket end 356 of outer sleeve 354 is then aligned over the top of receiver member 450, with clamping tips 358 aligned over flat sections 455 of receiver member. Socket end 356 is lowered over receiver member 50 until tabs 358a on clamping tips 358 pass over flat portions 455. Instrument 310 is then rotated relative to receiver 450 until tabs 358a move out of alignment with flat sections 455 and move underneath the round portions of ledges 451. Tabs 358a axially engage the ledges to lock socket end 356 to receiver 450.

Rotation of instrument 310 does not transfer torque to receiver member 450. Receiver 450 remains stationary in the implanted condition, and clamping tips 358 slide around ledges 451 without minimal or no friction. As shown in FIG. 15, clamping tips 358 are oriented at an angle with respect to the plane of the handles. That is, a plane extending through both clamping tips is transverse to the plane of the handles. The angular offset of the clamping tips 358 relative to the handles is such that the plane of the handles is not initially parallel to the rod when clamping tips 358 are aligned over flat sections 455. As instrument 310 is twisted to secure the clamping tips 358 to receiver 450, the plane of the handles moves into alignment with the rod. Therefore, the angular offset of clamping tips 358 corresponds to the angle of rotation used to secure socket end 356 to receiver 450. This angular offset may be relatively small, such as 30 degrees, so as to require a small amount of effort to lock the socket end onto the receiver. After rotation, the handles are aligned generally with the direction of the rod, and the pre-set orientation of the split in locking ring 90 is aligned with the U-shaped channels in receiver 450 to enhance locking engagement. In addition to strengthening and stabilizing the locking arrangement, this aligned condition places the handles vertically above the rod and maximizes the lateral work area around the rod and fixation assembly.

Once instrument 310 is secured to receiver 450, locking device 70 is advanced into the receiver. The second drive assembly featuring the twist knob 322 can be used to begin advancing the pusher member 326 and locking element 70 toward the distal end of outer sleeve 354. As locking element 70 initially advances through outer sleeve 354, locking element 70 is subject to minimal or no axial resistance. Twist knob 322 can be used to quickly traverse the length of outer sleeve 354 and introduce locking element 70 into receiver 450.

Referring to FIG. 33, receiver member 450 includes one or more converging sections or constrictions 461. Constrictions 461 form loading areas that gradually compress locking ring 90 into locking device 70, and in a step-wise manner as the locking element is advanced into receiver 450. Each constriction 461 represents a relatively small amount of compression of locking ring 90, and does not require splaying of receiver body 450. The passage of locking ring 90 through at least the first constriction 461 does not require great force. As locking element 70 is advanced further and further into receiver body 450, however, resistance gradually increases.

Once twist knob 322 is fully engaged, or once introduction of locking element 70 becomes too difficult to continue with the twist knob due to the increase in resistance, the user can operate the first drive mechanism to continue and complete the introduction. The gear assembly 360 provides substantially larger forces than the forces provided by the second drive assembly, with forces great enough to overcome is the resistance against advancement of locking element 70. Preferably, the dimensions of the components and the incremental spacing of constrictions 461 are set such that a majority of the introduction can be accomplished rapidly with the second actuating assembly. The remainder of the introduction distance is preferably accomplished with only a few pumps of the first drive assembly. Ideally, the front and rear handles 391, 346 are squeezed no more than five times to complete the introduction and locking of the locking device 70. A greater number of pumps may be needed, however, depending on factors such as the number of loading areas in the receiver member, and the desired position of the rod within the rod receiving channel.

Once locking device 70 reaches the locked position and the locking ring 90 snaps into a locked condition, the locking device is released from the pusher member 326. Pusher member 326 is under a significant load, and is disconnected using the second drive assembly. Switch lever 387 is moved to the reverse position, and the handles 391, 346 are squeezed to detach pusher member 326 from locking device. As forward handle 391 is squeezed toward rear handle 346, ratchet assembly 380 moves in unison with the forward handle, with the forward handle and ratchet assembly pivoting about an axis substantially aligned with hex hole 384. With switch 387 in the reverse setting, ratchet wheel 383 is locked against counter-rotation by pawl 385, which forces the ratchet wheel and hex hole 384 to rotate in unison with ratchet assembly and forward handle 391. The rotating hex hole 384 imparts torque to the hexagonal end 372a of worm 372 and rotates the worm. The worm 372, in turn, transfers torque to worm gear 362. The axial position of worm gear 362 is fixed between bearing bodies 365, such that the worm gear spins in place relative to rear handle assembly 340. Internal power thread 363 of worm gear 362 engages external power thread 333 of load shaft 330 during the rotation, causing an axial translation of the load shaft in the proximal direction. Load shaft 330, in turn, pulls pusher assembly 320 in the proximal direction by virtue of the threaded engagement between proximal section 331 and threaded pusher member 323. As pusher assembly 320 moves in the proximal direction, pusher member 326 is detached from the locking element and retracted into outer sleeve 354. Front handle 391 can be squeezed repeatedly to fully retract load shaft 330.

Pusher member 326 can be moved back to the fully retracted position within outer sleeve 354 by compressing the handles 391, 346 multiple times. Alternatively, the user can twist the knob 322 to retract the pusher member after squeezing the handle 391 a few times to complete the retraction. Once retraction is complete, socket end 356 of nose assembly 350 is twisted in the direction opposite to that used to secure it to receiver 450 until tabs 358a on clamping tips 358 align with flat sections 455. At this stage, tabs 358a are no longer axially restrained by ledges 451, permitting the instrument to be removed from receiver member 450.

The above method of operation is not intended to represent the only manner of operation, but is merely exemplary of how the instrument 310 and its components can function. Some steps may be added or omitted from the above-described sequence without departing from embodiments of the invention. There are advantages to operating the instrument 310 at certain orientations with respect to the rod direction and fixation assembly. For example, when the plane of the handles is oriented parallel to the direction of the rod (e.g. the handles are positioned vertically above the rod for a rod extending horizontally), the work area around the rod and fixation assembly is maximized.

Typical rod fixation systems are implanted with multiple polyaxial screws and rod receiving components. Multiple locking elements must be introduced and tightened down over the rod or rods at different screw locations. It may be desirable to use an introducer instrument that easily loads and reloads locking devices into the instrument. This can reduce the overall time required to complete implantation of the rod fixation system. For example, an exemplary instrument in accordance with the invention may include a magazine loader attached to the instrument for automatically loading locking elements onto the pusher member. A magazine loader may be formed integrally with one or more components of the instrument, or detachably connected with the instrument.

Figure 34:
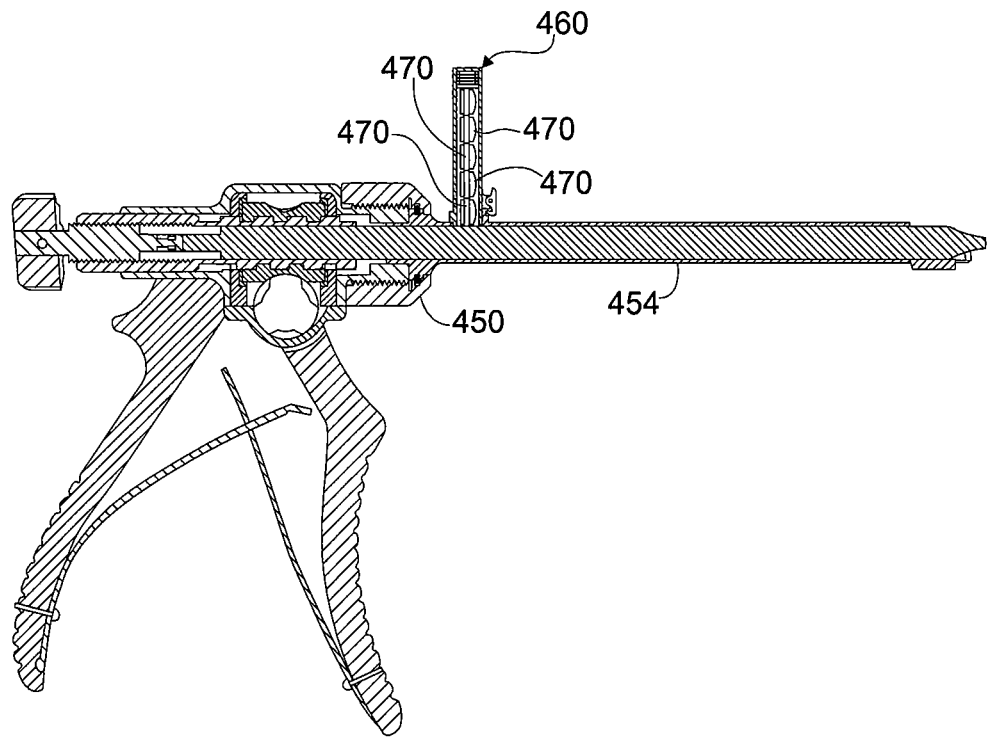
FIG. 34 is a right side cross-sectional view of the instrument in accordance with another embodiment of the invention.
Figure 35:
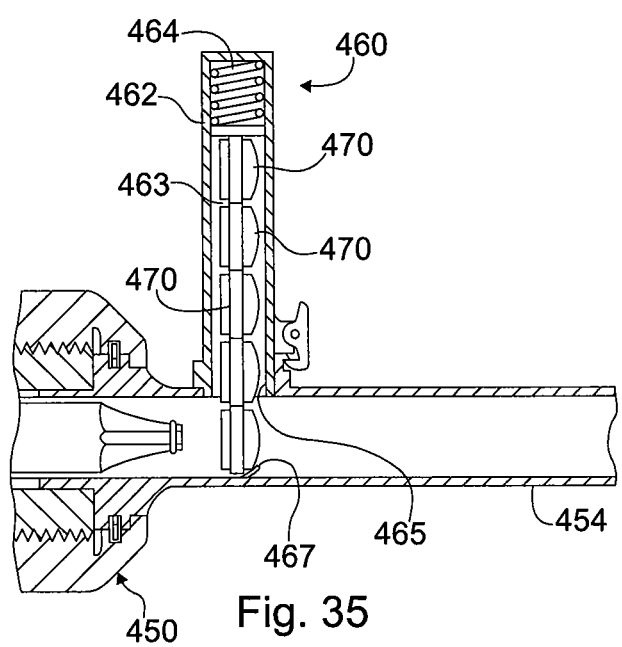
FIG. 35 is an enlarged truncated cross-sectional view of a portion of the instrument of FIG. 34.

Referring now to FIGS. 34 and 35, an exemplary instrument 410 in accordance with another embodiment of the invention includes a nose assembly 450 and outer sleeve 454 with one possible magazine loading mechanism 460. Magazine 460 includes an elongated housing 462 with an internal chamber 463 containing a series of locking devices 470. Housing 462 extends generally perpendicularly to outer sleeve 454. Chamber 463 interconnects with a bore in outer sleeve 454 through an opening 465. The series of locking elements 470 are stacked in the magazine and retained in the stacked position under compression by a biasing element 464. Biasing element 464 has sufficient stored energy to expand and eject all the locking elements from the magazine chamber 463. The stack of locking elements 470 are retained in the magazine 460 when pusher member 426 blocks opening 465. When pusher member 426 is retracted or removed from outer sleeve 450 and opening 465 is clear, biasing element 464 expands under the stored energy to eject a locking element out of chamber 463 and into outer sleeve 454. A flexible detent 467 or similar mechanism receives and holds each ejected locking element 470 in position to be engaged by the distal end of pusher member 426 to facilitate loading. Each locking element 470 is adapted to detachably receive and engage the distal end of pusher member 426 in response to advancement of the pusher member. Once a locking element 470 is loaded onto pusher member 426, the locking element 470 can be advanced distally over the flexible detent 467. The next locking element in the stack is retained in chamber 463 until pusher member is again retracted proximally so as to clear opening 465. Magazine 460 may be located at any section along outer sleeve, or interconnected with other components of the instrument, such as the rear handle assembly, for example.

While preferred embodiments of the invention have been shown and described herein, it will be understood that such embodiments are provided by way of example only. Numerous variations, changes and substitutions will occur to those skilled in the art without departing from the scope of the invention. Accordingly, it is intended that the appended claims cover all such variations as fall within the scope of the invention.

What is claimed:

1. A fixation assembly for an elongated spinal fixation member, the fixation assembly comprising:
   A. a receiver component comprising:
      a generally cylindrical receiver body having an outermost circumferential surface and a pair of arms, the pair of arms defining an annular groove on an inner surface of the receiver body; and
      two ledges projecting radially outwardly from the outermost circumferential surface of the receiver body,
      each ledge including two arcuate perimetric regions defining rounded portions facing radially outwardly and a flat perimetric region defining a flat portion facing radially outwardly and extending between the rounded portions,
      the flat portions of the ledges being diametrically opposed to one another with each flat portion projecting in a radially outward direction beyond the outermost circumferential surface of the receiver body,
      the ledges being separated from one another by a pair of slots extending longitudinally along a length of the receiver body between the ledges,
      each arm extending away from an upper surface of a corresponding ledge and in a direction along the length of the receiver body, wherein an outermost circumference of the pair of arms is less than an outermost circumference of the two ledges, and
   B. a locking mechanism comprising:
      a generally cylindrical cap comprising an outer wall which defines an annular recess;
      a locking ring formed of a resilient flexible material, the locking ring positioned in the annular recess and around a circumference of the cap, the locking ring including an inner face that opposes and is separated from an end wall of the annular recess by a radial clearance when the locking ring is in a relaxed condition,
      the locking ring being deformable between a radially compressed condition, in which the locking ring is pressed inwardly into the annular recess, and a radially expanded condition, in which an outer portion of the locking ring extends outwardly from the recess,
      the annular groove of the receiver component being sized to receive the outer portion of the locking ring when the annular recess of the locking ring opposes the annular groove of the receiver body.

2. The fixation assembly of claim 1, wherein each flat portion includes a bore defined therein.

3. The fixation assembly of claim 2, wherein the bores are centrally located on their respective flat portions, diametrically opposite one another on the receiver body.

4. The fixation assembly of claim 1, wherein the rounded portions are circular.

5. The fixation assembly of claim 1, wherein each flat portion is centered between the two corresponding arcuate perimetric regions.

6. The fixation assembly of claim 1 further comprising a release aperture extending through the receiver component, the release aperture being axially aligned with the annular groove to provide access to the locking ring when the locking ring is received in the annular groove in the receiver component.

7. A fixation assembly for an elongated spinal fixation member, the fixation assembly comprising:
   A. a receiver component comprising:
      a receiver body comprising an outermost circumferential surface and a pair of arms, the pair of arms defining an annular groove on an inner surface of the body; and
      two rounded ledges projecting radially outwardly from the outermost circumferential surface of the receiver body,
      each rounded ledge including two arcuate perimetric regions defining rounded portions facing radially outwardly and a flat perimetric region defining a flat portion facing radially outwardly and extending between the rounded portions,
      the flat portions of the rounded ledges being diametrically opposed to one another with each flat portion projecting in a radially outward direction beyond the outermost circumferential surface of the receiver body,
      the rounded ledges being separated from one another by a pair of slots defined between the ledges,
      each arm extending away from an upper surface of a corresponding ledge and in a direction along the length of the receiver body, wherein an outermost circumference of the pair of arms is less than an outermost circumference of the two ledges, and
   B. a locking mechanism comprising:
      a generally cylindrical cap comprising an outer wall which defines an annular recess;
      a locking ring formed of a resilient flexible material, the locking ring positioned in the annular recess and around a circumference of the cap, the locking ring including an inner face that opposes and is separated from an end wall of the annular recess by a radial clearance when the locking ring is in a relaxed condition,
      the locking ring being deformable between a radially compressed condition, in which the locking ring is pressed inwardly into the annular recess, and a radially expanded condition, in which an outer portion of the locking ring extends outwardly from the recess, the annular groove of the receiver body being sized to receive the outer portion of the locking ring when the annular groove of the locking ring is axially aligned with the annular groove of the receiver body.

8. The fixation assembly of claim 7, wherein each flat portion includes a bore defined therein and extending radially inwardly into the receiver component.

9. The fixation assembly of claim 8, wherein the bores are centrally located in their respective flat portions, diametrically opposite one another on the receiver component.

10. The fixation assembly of claim 7, wherein the rounded portions are circular.

11. The fixation assembly of claim 7, wherein each flat portion is centered between the two corresponding rounded portions.

12. The fixation assembly of claim 7, wherein each ledge extends perpendicularly to a longitudinal axis of the receiver body.

13. The fixation assembly of claim 7 further comprising a release aperture extending through the receiver component, the release aperture being axially aligned with the annular groove to provide access to the locking ring when the locking ring is received in the annular groove in the receiver component.

14. A fixation assembly for an elongated spinal fixation member, the fixation assembly comprising:

A. a receiver component comprising:

a generally cylindrical receiver body having a socket therein, the receiver body having an outermost circumferential surface and a pair of arms, the pair of arms defining an annular groove on an inner surface of the receiver body; and two ledges projecting radially outwardly from the outermost circumferential surface of the receiver body, each ledge including two arcuate perimetric regions defining rounded portions facing radially outwardly and a flat perimetric region defining a flat portion facing radially outwardly and extending between the rounded portions, the flat portions of the ledges being diametrically opposed to one another, with each flat portion projecting in a radially outward direction beyond the outermost circumferential surface of the receiver body, the ledges being separated from one another by a pair of slots extending longitudinally along the receiver body between the ledges, the slots being diametrically opposed to one another and defining a channel for receiving a rod which extends through the socket and between the ledges in a direction generally perpendicular to a longitudinal axis of the body, each arm extending away from an upper surface of a corresponding ledge and in a direction along the length of the receiver body, wherein an outermost circumference of the pair of arms is less than an outermost circumference of the two ledges, and B. a locking mechanism comprising:

a generally cylindrical cap comprising an outer wall which defines an annular recess, the annular recess extending radially inward toward a longitudinal axis of the cap and terminating at an end wall;

a locking ring formed of a resilient flexible material, the locking ring positioned in the annular recess and around a circumference of the cap, the locking ring including an inner face that is separated from the end wall of the annular recess by a radial clearance when the locking ring is in a relaxed condition, the locking ring being deformable between a radially compressed condition, in which the locking ring is pressed inwardly into the annular recess, and a radially expanded condition, in which an outer portion of the locking ring extends outwardly from the recess, the annular groove inside the receiver component being sized to receive the outer portion of the locking ring when the locking ring is axially aligned with the annular groove.

15. The fixation assembly of claim 14, wherein each flat portion includes a bore defined therein.

16. The fixation assembly of claim 15, wherein the bores are centrally located on their respective flat portions, diametrically opposite one another on the receiver body.

17. The fixation assembly of claim 14, wherein the rounded portions are circular.

18. The fixation assembly of claim 14, wherein each flat portion is centered between the two corresponding rounded portions.

19. The fixation assembly of claim 14 further comprising a release aperture extending through the receiver component, the release aperture being axially aligned with the annular groove to provide access to the locking ring when the locking ring is received in the annular groove in the receiver component.

* * * * *